(12) United States Patent
Blair et al.

(10) Patent No.: US 11,882,992 B2
(45) Date of Patent: *Jan. 30, 2024

(54) COMPOSITE TISSUE MARKERS DETECTABLE VIA MULTIPLE DETECTION MODALITIES INCLUDING RADIOPAQUE ELEMENT

(71) Applicant: VIEW POINT MEDICAL, INC., Carlsbad, CA (US)

(72) Inventors: William Blair, San Diego, CA (US); Mike Jones, San Clemente, CA (US); John Merritt, San Clemente, CA (US)

(73) Assignee: VIEW POINT MEDICAL, INC., Carlsbad, CA (US)

( * ) Notice: Subject to any disclaimer, the term of this patent is extended or adjusted under 35 U.S.C. 154(b) by 66 days.

This patent is subject to a terminal disclaimer.

(21) Appl. No.: 17/102,761

(22) Filed: Nov. 24, 2020

(65) Prior Publication Data

US 2021/0153972 A1 May 27, 2021

Related U.S. Application Data

(60) Provisional application No. 63/073,285, filed on Sep. 1, 2020, provisional application No. 62/941,337, filed on Nov. 27, 2019.

(51) Int. Cl.
*A61B 90/00* (2016.01)

(52) U.S. Cl.
CPC ........ *A61B 90/39* (2016.02); *A61B 2090/392* (2016.02); *A61B 2090/3925* (2016.02); *A61B 2090/3954* (2016.02); *A61B 2090/3966* (2016.02); *A61B 2090/3995* (2016.02)

(58) Field of Classification Search
CPC ..................................................... A61B 90/39
See application file for complete search history.

(56) References Cited

U.S. PATENT DOCUMENTS

| 5,512,094 A | 4/1996 | Linton |
| 6,161,034 A | 12/2000 | Burbank et al. |

(Continued)

FOREIGN PATENT DOCUMENTS

| CN | 102389576 A | 3/2012 |
| CN | 103803556 A | 5/2014 |

(Continued)

OTHER PUBLICATIONS

Kamaya et al., Twinkling artifact on color Doppler sonography: dependence on machine parameters and underlying cause, AJR Am J Roentgenol. Jan. 2003; 180(1):215-22. doi: 10.2214/ajr.180.1. 1800215. (Year: 2003).

(Continued)

*Primary Examiner* — Angela M Hoffa
*Assistant Examiner* — Younhee Choi
(74) *Attorney, Agent, or Firm* — Cozen O'Connor

(57) ABSTRACT

Composite markers employ a gel carrier to carry at least one radiopaque element (e.g., wire or band or clip) and one or more other contrast materials, each detectable by a detection modality different than one another. Methods for forming these composite markers and methods of marking a target site in a mammalian subject employing these composite markers are also discussed herein.

32 Claims, 11 Drawing Sheets

(56) References Cited

U.S. PATENT DOCUMENTS

| | | | |
|---|---|---|---|
| 6,174,330 | B1* | 1/2001 | Stinson ............... A61L 27/50 606/198 |
| 6,221,326 | B1 | 4/2001 | Amiche |
| 6,235,801 | B1 | 5/2001 | Morales et al. |
| 6,331,166 | B1 | 12/2001 | Burbank et al. |
| 6,347,241 | B2 | 2/2002 | Burbank et al. |
| 6,427,081 | B1 | 7/2002 | Burbank et al. |
| 6,494,841 | B1 | 12/2002 | Thomas et al. |
| 6,567,689 | B2 | 5/2003 | Burbank et al. |
| 6,699,206 | B2 | 3/2004 | Burbank et al. |
| 6,725,083 | B1 | 4/2004 | Burbank et al. |
| 6,862,470 | B2 | 3/2005 | Burbank et al. |
| 6,996,433 | B2 | 2/2006 | Burbank et al. |
| 7,322,938 | B2 | 1/2008 | Burbank et al. |
| 7,322,939 | B2 | 1/2008 | Burbank et al. |
| 7,322,940 | B2 | 1/2008 | Burbank et al. |
| 7,651,505 | B2 | 1/2010 | Lubock et al. |
| 7,792,569 | B2 | 9/2010 | Burbank et al. |
| 7,871,438 | B2 | 1/2011 | Corbitt |
| 7,970,454 | B2 | 6/2011 | Jones et al. |
| 7,983,734 | B2 | 7/2011 | Jones et al. |
| 8,157,862 | B2 | 4/2012 | Corbitt |
| 8,177,792 | B2 | 5/2012 | Lubock et al. |
| 8,219,182 | B2 | 7/2012 | Burbank et al. |
| 8,224,424 | B2 | 7/2012 | Burbank et al. |
| 8,361,082 | B2 | 1/2013 | Jones et al. |
| 8,440,229 | B2 | 5/2013 | Trogler et al. |
| 8,498,693 | B2 | 7/2013 | Jones et al. |
| 8,626,269 | B2 | 1/2014 | Jones et al. |
| 8,626,270 | B2 | 1/2014 | Burbank et al. |
| 8,668,737 | B2 | 3/2014 | Corbitt |
| 8,680,498 | B2 | 3/2014 | Corbitt et al. |
| 8,718,745 | B2 | 5/2014 | Burbank et al. |
| 8,784,433 | B2 | 7/2014 | Lubock et al. |
| 8,880,154 | B2 | 11/2014 | Jones et al. |
| 9,044,162 | B2 | 6/2015 | Jones et al. |
| 9,149,341 | B2 | 10/2015 | Jones et al. |
| 9,220,585 | B2 | 12/2015 | Horton et al. |
| 9,327,061 | B2 | 5/2016 | Govil et al. |
| 9,480,554 | B2 | 11/2016 | Corbitt |
| 9,579,077 | B2 | 2/2017 | Casanova et al. |
| 9,743,909 | B1 | 8/2017 | Sapozhnikov et al. |
| 9,801,688 | B2 | 10/2017 | Jones et al. |
| 9,820,824 | B2 | 11/2017 | Jones et al. |
| 9,861,294 | B2 | 1/2018 | Jones et al. |
| 10,172,674 | B2 | 1/2019 | Jones et al. |
| 2003/0204137 | A1 | 10/2003 | Chesbrough et al. |
| 2004/0116806 | A1 | 6/2004 | Burbank et al. |
| 2004/0187524 | A1 | 9/2004 | Sen et al. |
| 2004/0236213 | A1 | 11/2004 | Jones et al. |
| 2005/0008578 | A1 | 1/2005 | Schmidt |
| 2005/0158390 | A1 | 7/2005 | Rana et al. |
| 2006/0079597 | A1* | 4/2006 | Muratoglu ............... C08J 3/28 522/178 |
| 2006/0293581 | A1 | 12/2006 | Plewes et al. |
| 2007/0276252 | A1 | 11/2007 | Kolasa et al. |
| 2008/0097207 | A1 | 4/2008 | Cai |
| 2011/0196285 | A1 | 8/2011 | Chen et al. |
| 2011/0229576 | A1 | 9/2011 | Trogler et al. |
| 2012/0052012 | A1 | 3/2012 | Chenite et al. |
| 2012/0059376 | A1* | 3/2012 | Rains ............... A61B 17/80 606/62 |
| 2013/0039848 | A1 | 2/2013 | Bradbury et al. |
| 2013/0066195 | A1 | 3/2013 | Sirimanne et al. |
| 2013/0230570 | A1 | 9/2013 | Trogler et al. |
| 2014/0017130 | A1 | 1/2014 | Trogler et al. |
| 2014/0187911 | A1 | 7/2014 | Bolan et al. |
| 2014/0243675 | A1 | 8/2014 | Burbank et al. |
| 2015/0057546 | A1 | 2/2015 | Yoon et al. |
| 2015/0143688 | A1 | 5/2015 | Garbini et al. |
| 2015/0173848 | A1 | 6/2015 | Bolan et al. |
| 2015/0273061 | A1 | 10/2015 | Trogler et al. |
| 2016/0051337 | A1 | 2/2016 | Bolan et al. |
| 2016/0143624 | A1 | 5/2016 | Liberman et al. |
| 2016/0151124 | A1 | 6/2016 | Domb et al. |
| 2016/0346404 | A1 | 12/2016 | Trogler et al. |
| 2017/0066162 | A9 | 3/2017 | Fisher |
| 2017/0209601 | A1 | 7/2017 | Kumar et al. |
| 2017/0368209 | A1 | 12/2017 | Alqathami |
| 2018/0021102 | A1 | 1/2018 | Azizian et al. |
| 2018/0065859 | A1 | 3/2018 | Kummel et al. |
| 2018/0092987 | A1 | 4/2018 | Trogler et al. |
| 2018/0280111 | A1 | 10/2018 | Parish |
| 2018/0289444 | A1 | 10/2018 | Blair et al. |
| 2019/0176372 | A1 | 6/2019 | Fisher et al. |
| 2019/0192253 | A1 | 6/2019 | Yang et al. |
| 2019/0365345 | A1 | 12/2019 | Byram et al. |

FOREIGN PATENT DOCUMENTS

| | | | |
|---|---|---|---|
| CN | 105377243 | A | 3/2016 |
| JP | 2013536024 | A | 9/2013 |
| JP | 2016505475 | A | 2/2016 |
| JP | 2016516729 | A | 6/2016 |
| JP | 6898603 | B2 | 6/2021 |
| KR | 20150063097 | A | 6/2015 |
| WO | 0110302 | A3 | 8/2001 |
| WO | 2006105353 | A2 | 10/2006 |
| WO | 2009023697 | A2 | 2/2009 |
| WO | 2012142625 | A2 | 10/2012 |
| WO | 2014052911 | A1 | 4/2014 |
| WO | 2016149711 | A1 | 9/2016 |
| WO | 2018097891 | A1 | 5/2018 |
| WO | 2018187594 | A2 | 10/2018 |
| WO | 2019067441 | A1 | 4/2019 |
| WO | WO-2019243419 | A1 * | 12/2019 ............. A61B 90/39 |

OTHER PUBLICATIONS

European Search Report issued in European Application No. 18781390. 2, dated Jan. 19, 2021, 8 pages.

Gorsd, Marina N. et al., "Synthesis and characterization of hollow silica spheres", Procedia Material Science, 2015, vol. 8, pp. 567-576.

International Preliminary Report on Patentability dated Feb. 16, 2010 in International Application No. PCT/US2008/072972 filed: Aug. 13, 2008 and published as: WO 2009/023697 on Feb. 19, 2009, 7 pages.

International Preliminary Report on Patentability dated Mar. 1, 2016 in International Application No. PCT/US2014/052911 filed: Aug. 27, 2014 and published as: WO 2015/031482 on Mar. 1, 2015, 9 pages.

International Preliminary Report on Patentability dated Sep. 19, 2017 in International Application No. PCT/US2016/023492 filed: Mar. 21, 2016 and published as: WO 2016/149711 on Sep. 22, 2016, 6 pages.

International Search Report & Written Opinion issued in Application No. PCT/US2020/048023, dated Dec. 9, 2020, 17 pages.

International Search Report and Written Opinion dated Aug. 16, 2016 in International Application No. PCT/US2016/023492 filed: Mar. 21, 2016 and published as: WO 2016/149711 on Sep. 22, 2016, 9 pages.

International Search Report and Written Opinion dated Dec. 3, 2018 in International Application No. PCT/US2018/026291 filed: April, 5, 2018 and published as: WO/2018/187594 on: Oct. 11, 2018.

International Search Report and Written Opinion dated Feb. 19, 2009 in International Application No. PCT/US2008/072972 filed: Aug. 13, 2008 and published as: WO 2009/023697 on Feb. 19, 2009, 9 pages.

International Search Report and Written Opinion dated Oct. 3, 2015 in International Application No. PCT/US2014/052911 filed: Aug. 27, 2014 and published as: WO 2015/031482 on Mar. 5, 2015, 14 pages.

International Search Report and Written Opinion, dated Apr. 6, 2021 2021, in International Application No. PCT/US2020/062322, 20 pages.

International Search Report and Written Opinion, dated Mar. 24, 2021, in International Application No. PCT/US2020/062272, 12 pages.

(56) References Cited

OTHER PUBLICATIONS

Office Action issued in Japanese Patent Application No. 2019-555229, dated Dec. 24, 2020, 8 pages.
Arnal, Pablo M, et al., "High-temperature-stable catalysts by hollow sphere encapsulation," Angew Chem Int Ed Engl. Dec. 4, 2006;45(48):8224-7.
Brinker, C.J., "Hydrolysis and Condensation of Silicates: Effects on Structure", Journal of Non-Crystalline Solids, vol. 100, 1988, pp. 31-50.
Bunker, Christopher E, et al., "Low-Temperature Stability and High-Temperature Reactivity of Iron-Based Core-Shell Nanoparticles", J. Am. Chem. Soc., 2004, vol. 126, No. 35, pp. 10852-10853.
Caruntu, Daniela , et al., "Synthesis of Variable-Sized Nanocrystals of Fe3O4 with High Surface Reactivity." Chemistry of Materials, vol. 16(25), pp. 5527-5534. (Year: 2004).
Caruso, Frank , et al., "Electrostatic Self-Assembly of Silica Nanoparticle-Polyelectrolyte Multilayers on Polystyrene Latex Particles," J. Am. Chem. Soc., 1998, 120 (33), pp. 8523-8524.
Caruso, Frank , et al., "Magnetic Nanocomposite Particles and Hollow Spheres constructed by a Sequential Layering Approach." Chemistry of Materials, vol. 13, pp. 109-116. (Year: 2001).
Caruso, Frank , et al., "Nanoengineering of Inorganic and Hybrid Hollow Spheres by Colloidal Templating," Science Nov. 6, 1998: vol. 282, Issue 5391, pp. 1111-1114.
Cha, Jennifer N, et al., "Biomimetic synthesis of ordered silica structures mediated by block copolypeptides", Nature, vol. 403, Issue 6767, pp. 289-292 (2000).
Chang, Song-Yuan , et al., "Preparation and Properties of Tailored Morphology, Monodisperse Colloidal Silica-Cadmium Sulfide Nanocomposites,", J. Am. Chem. Soc., Jul. 1994, 116 (15), pp. 6739-6744.
Cornelissen, Jeroen J.L.M, et al., "Versatile synthesis of nanometer sized hollow silica spheres," Chem. Commun., 2003,8, 1010-1011.
Ding, Xuefeng , et al., "A novel approach to the synthesis of hollow silica nanoparticles," Materials Letters 2004, 58(27-28), 3618-3621.
Huang, Chih-Chia , et al., "Shell-by-shell synthesis of multi-shelled mesoporous silica nanospheres for optical imaging and drug delivery", Biomaterials, 32, 556-564,. (Year: 2011).
Jin, Pu , et al., "Synthesis and catalytic properties of nickel-silica composite hollow nanospheres." J Phys Chem B. May 1, 2004;108(20):6311-4. doi: 10.1021/jp049754g.
Kato, Noritaka , et al., "Synthesis of monodisperse mesoporous silica hollow microcapsules and their release of loaded materials." Langmuir. Sep. 7, 2010;26(17):14334-44. doi: 10.1021/la1024636.
Kempen, Paul J, et al., "Theranostic Mesoporous Silica Nanoparticles Biodegrade after Pro-Survival Drug Delivery and Ultrasound/Magnetic Resonance Imaging of Stem Cells." Theranostics 2015: 5(6) 631-642.
Lee, Jeongwoo , et al., "Synthesis of polystyrene/silica composite particles by soap-free emulsion polymerization using positively charged colloidal silica." J Colloid Interface Sci. Jun. 2007 A181;310(1):112-20. Epub Feb. 15, 2007.
Li, Xin , et al., "Formation of Gold Nanostar-Coated Hollow Mesoporous Silica for Tumor Multimodality Imaging and Photothermal Therapy", 5817-5827.
Liberman, Alexander , et al., "Color Doppler Ultrasound and gamma imaging of intratumorally injected 500nm iron-silica nanoshells" ACS Nano, Jul. 23, 2013, 7(7) 6367-6377.
Liberman, Alexander , et al., "Hollow iron-silica nanoshells for enhanced high intensity focused ultrasound" J Surg Res, May 10, 2014, 190(2): 391-398.
Liberman, Alexander , et al., "Mechanically tunable hollow silica ultrathin nanoshells for ultrasound contrast agents" Adv Funct Mater, 25(26) 4049-4057, May 21, 2015.
Liu, Jian , et al., "From Hollow Nanosphere to Hollow Microsphere: Mild Buffer Provides Easy Access to Tunable Silica Structure," J. Phys. Chem. C 2008, 112(42), pp. 16445-16451.
Lu, Yu , et al., "Synthesis and crystallization of hybrid spherical colloids composed of polystyrene cores and silica shells," Langmuir, American Chemical Society, 2004, pp. 3464-3470, vol. 20, No. 8.

Mallery, Susan R., et al., Susan R. Mallery et al. Formulation and In-Vitro and In-Vivo Evaluation of a Mucoadhesive Gel Containing Freeze Dried Black Raspberries: Implications for Oral Cancer Chemoprevention, Pharma Res. 24(4), 728-737. (Year: 2007).
Martinez, Paul H, et al., Martinez et al., "Hard shell gas-filled contrast enhancement particles for colour Doppler ultrasound imaging of tumors" Medchemcomm, Oct. 1, 2010(4) 266-270.
Mitchell , et al., "Iron(III)-Doped, Silica Nanoshells: A Biodegradable Form of Silica" J.Am. Chem. Soc. 2012, 34, 13997-14003 (Year: 2021).
Mori, Hideharu , et al., "Organic-Inorganic Nanoassembly Based on Complexation of Cationic Silica Nanoparticles and Weak Anionic Polyelectrolytes in Aqueous and Alcohol Media," Langmuir, vol. 20(5), 2004, pp. 1934-1944.
Nandiyanto, Asep Bayu Dani, et al., "Mesopore-Free Hollow Silica Particles with Controllable Diameter and Shell Thickness Via Additive-Free Synthesis." Langmuir. Jun. 12, 2012;28(23):8616-24. doi: 10.1021/la301457v. Epub May 31, 2012.
Paefgen, Vera , "Evolution of contrast agents for ultrasound imaging and ultrasound-mediated drug delivery," Front Pharmacol 2015, 6, 197.
Parida, Sudam K, et al., "Adsorption of organic molecules on silica surface," Advances in Colloid and Interface Science, 2006, vol. 121, Issue: 1-3, pp. 77-110.
Slowing, Igor I, et al., . "Mesoporous Silica Nanoparticles for Drug Delivery and Biosensing Applications," Adv. Funct. Mater., vol. 17, Issue 8 Apr. 2007 pp. 1225-1236.
Su, Yang , et al., "Synthesis of hierarchical hollow silica microspheres containing surface nanoparticles employing the quasi-hard template of poly(4-vinylpyridine) microspheres." Langmuir. Jul. 19, 2011;27 (14):8983-9. doi: 10.1021/la2014573. Epub Jun. 23, 2011.
Ta, Casey N., et al., "Integrated processing of contrast pulse sequencing ultrasound imaging for enhanced active contrast of hollow gas filled silica nanoshells and microshells," J. Vac. Sci. Technol. B 30(2), Mar./Apr. 2012, 6 pages.
Tada, Dayane B, et al., "Methylene Blue-Containing Silica-Coated Magnetic Particles: A Potential Magnetic Carrier for Photodynamic Therapy", Langmuir, 23, 8194-8199. (Year: 2007).
Tissot, Isabelle , et al., "Hybrid Latex Particles Coated with Silica," Macromolecules, Jun. 7, 2001, 34 (17), pp. 5737-5739.
Van Bommel, Kjeld J.C, et al., "Poly(L-lysine) Aggregates as Templates for the Formation of Hollow Silica Spheres," Adv. Mater. vol. 13, Issue 19, Oct. 2001, pp. 1472-1476.
Velikov, Krassimir P, et al., "Synthesis and Characterization of Monodisperse Core-Shell Colloidal Spheres of Zinc Sulfide and Silica," Langmuir, Jul. 10, 2001, 17 (16), pp. 4779-4786.
Voss, R.K. , "Doppler Ultrasound-Visible Signal Mark Microspheres are Better Identified than HydroMARK® Clips in a Simulated Intraoperative Setting in Breast and Lung Cancer," Presented at Society of Surgical Oncology meeting Chicago Illinois, Mar. 21-24, 2018.
Wang, H. , "Spherical silicon-shell photonic band gap structures fabricated by laser-assisted chemical vapor deposition," J. Appl. Phys. 2007, 101, 033129, Published Online: Feb. 15, 2007 Accepted: Dec. 2006.
Ward, Erin , et al., "Utilization of Iron (III) Doped Nanoshells for in vivo Marking of Non-palpable Tumors using VX2 Rabbit Model." Am. J. Surg., Dec. 2016, 212(6): 1140-1146.
Wu, Dazhen , et al., "Novel One-Step Route for Synthesizing CdS/Polystyrene Nanocomposite Hollow Spheres," Langmuir May 26, 2004, 20, (13), pp. 5192-5195.
Wu, W. , et al., "Synthesis of magnetic hollow silica using polystyrene bead as a template." Journal of Magnetism and Magnetic Materials, vol. 311(2), pp. 578-582, available online Sep. 22, 2006.
Xu, Xiangling , et al., "Synthesis and utilization of monodisperse hollow polymeric particles in photonic crystals" J Am Chem Soc. Jun. 4, 2004;126(25):7940-5.
Yao, Hiroshi , et al., "Electrolyte Effects on CdS Nanocrystal Formation in Chelate Polymer Particles: Optical and Distribution Properties", Langmuir 1998, 14(3), 595-601.
Yildirim, Adem , et al., "Stable Encapsulation of Air in Mesoporous Silica Nanoparticles: Fluorocarbon-Free Nanoscale Ultrasound Contrast Agents," Adv Healthc Mater. Jun. 2016; 5(11): 1290-1298.

(56) References Cited

OTHER PUBLICATIONS

Zhang, Kun, et al., "Double-scattering/reflection in a Single Nanoparticle for intensified Ultrasound Imaging," Sci Rep, 2015 5:8766.

Zhong, Ziyi, et al., "Preparation of mesoscale hollow spheres of TiO2 and SnO2 by templating against crystalline arrays of polystyrene beads," Adv. Mater. 2000, 12(3), 206-209.

Zhou, W., et al., "Drug-loaded, magnetic, hollow silica nanocomposites for nanomedicine." Nanomedicine: Nanotechnology, Biology and Medicine, vol. 1(3),2005, pp. 233-237.

Zhou, Dejian, et al., "Influence of the Foundation Layer on the Layer-by-Layer Assembly of Poly-L-lysine and Poly (styrenesulfonate) and Its Usage in the Fabrication of 3D Microscale Features." Langmuir, vol. 20(21), 2004, pp. 9089-9094.

Zhu, Yufang, et al., "Stimuli-responsive controlled drug release from a hollow mesoporous silica sphere/polyelectrolyte multilayer core-shell structure," Angew Chem Int Ed Engl. Aug. 12, 2005;44(32):5083-7.

First Office Action dated Nov. 9, 2021 for CN201880023936.2, with translation, 24 pages.

Hu et al., "Facile synthesis of amino-functionalized hollow silica microspheres and their potential application for ultrasound imaging, He Hu et al," Journal of Colloid and Interface Science, vol. 358, pp. 392-398, 2011.

Lu et al., "Synthesis of hollow silica microspheres and their applications in ultrasound imaging", Journal of Shanghai Normal University, vol. 41, Issue 4, pp. 432-439, 2012.

Notice of Reasons for Rejection, issued in corresponding Japanese Application No. 2021-063419, dated Apr. 11, 2022, 4 pages (English Translation).

Non Final Office Action for U.S. Appl. No. 17/102,758, dated Dec. 22, 2022, 23 pages.

Extended European Search Report for 20891745.0, dated Nov. 17, 2022, 8 pages.

Extended EP Search Report dated Nov. 17, 2022, EP App No. 20891874.8-1122, 7 pages.

EP Search Report dated Jul. 20, 2023 EP App No. 20857267-1126/4021306 PCT/US2020048025, 10 pages.

Richard Barr et al: "Artifiacts in diagnostic ultrasound, Reports in Medical Imaging", Jun. 1, 2013, p. 29, xp0555514374, DOI: 10.2147/RMI.S33464, pp. 41-42.

* cited by examiner

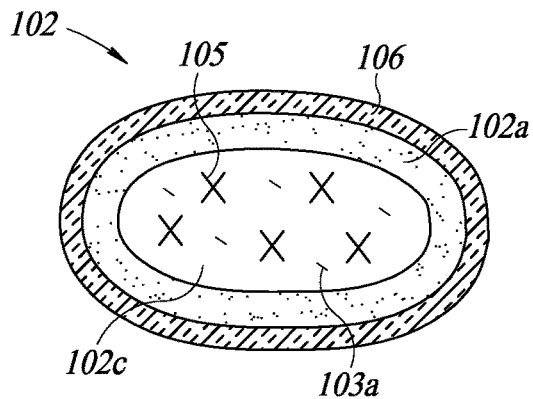
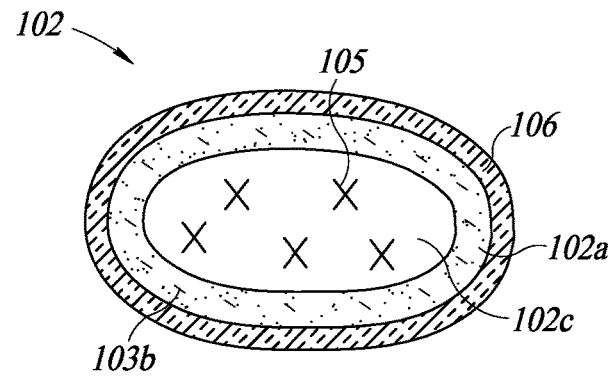
FIG. 2A  FIG. 2B
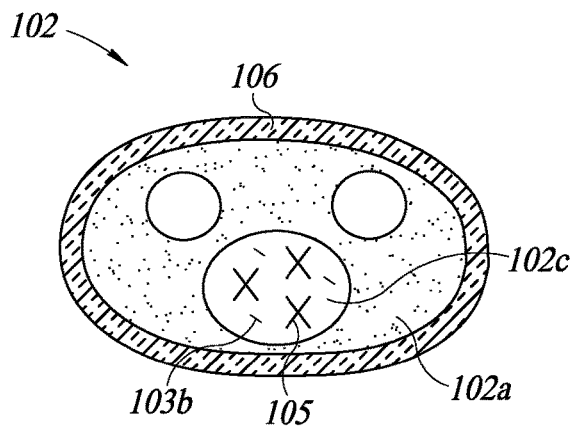
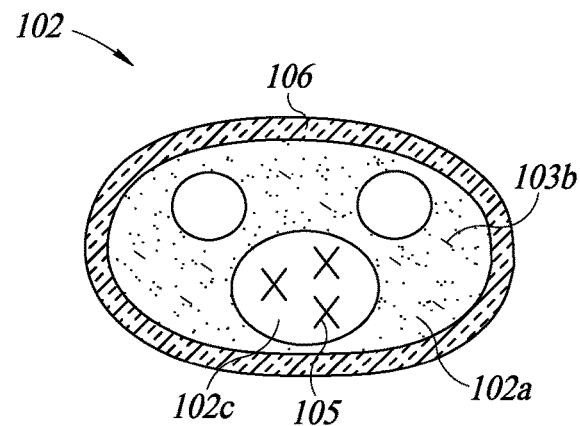
FIG. 2C  FIG. 2D
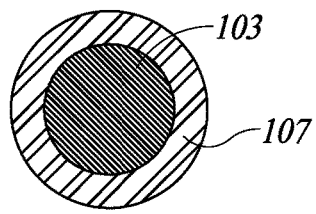
FIG. 3

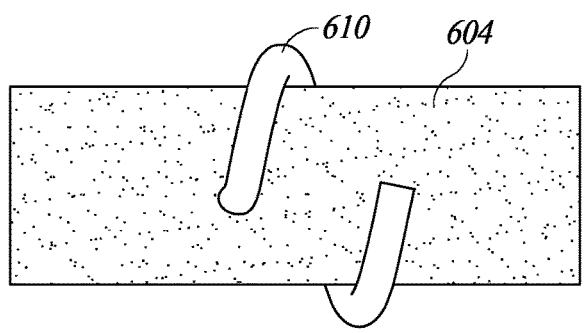
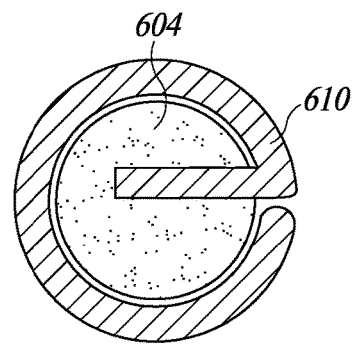
FIG. 6A  FIG. 6B
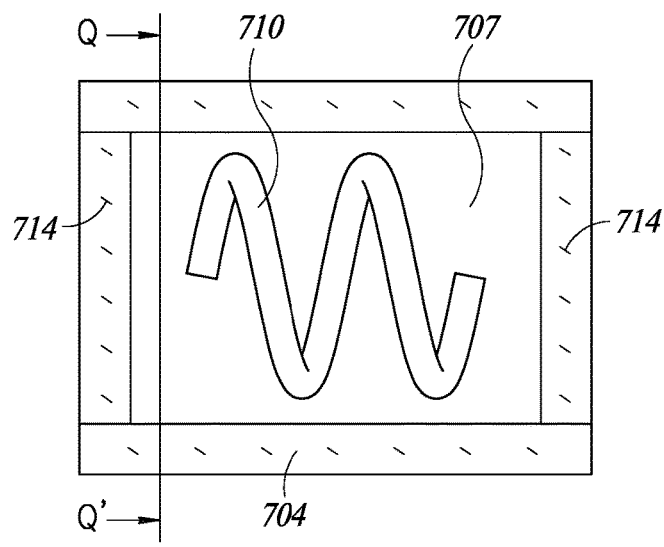
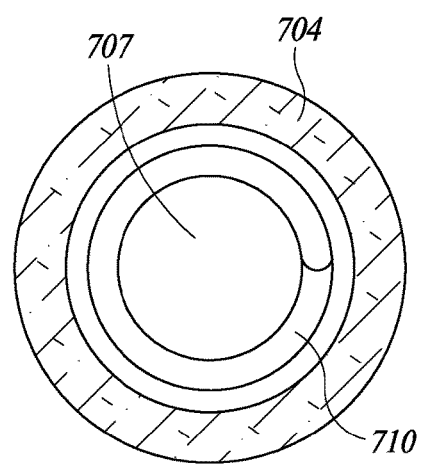
FIG. 7A  FIG. 7B

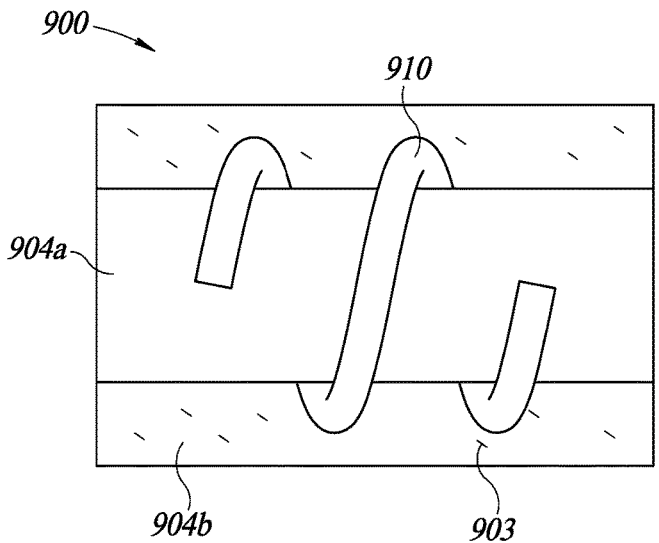 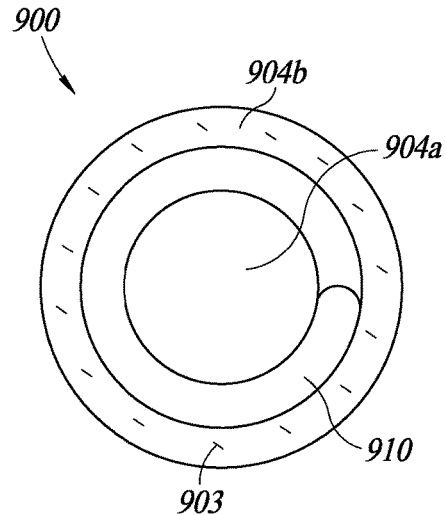
FIG. 9A    FIG. 9B
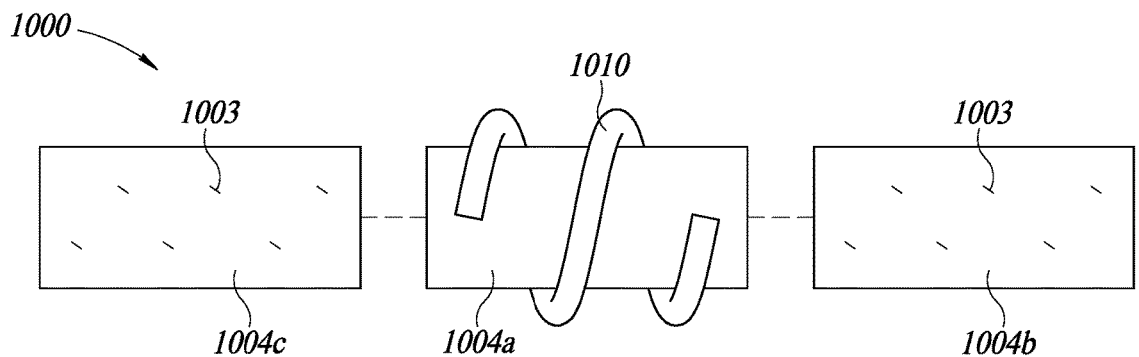
FIG. 10
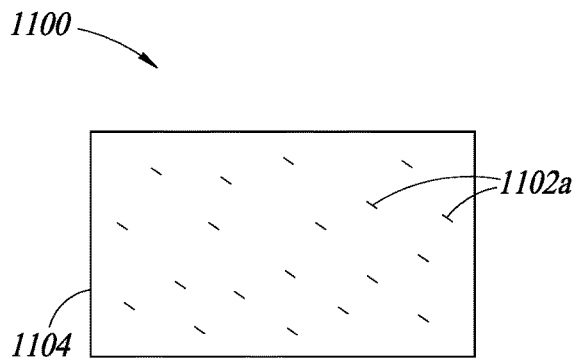 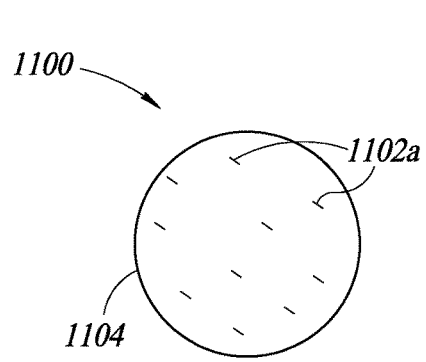
FIG. 11A    FIG. 11B

COMPOSITE TISSUE MARKERS DETECTABLE VIA MULTIPLE DETECTION MODALITIES INCLUDING RADIOPAQUE ELEMENT

BACKGROUND

Technical Field

This disclosure generally relates to the field of tissue markers and detection of tissue markers, and in particular to composite tissue markers comprising a gel carrier carrying at least one radiopaque element (e.g., radiopaque wire or band or clip) and one or more other contrast materials.

Description of the Related Art

Various types of tissue markers exist for identifying, locating, and marking bodily tissues over time and for assisting in the biopsy, excision, or ablation of the marked bodily tissue. Current diagnostic and therapeutic protocols, including cancer diagnostic and treatment (e.g., surgical procedures, radiation treatment), are impeded by existing tissue marker technology for localization of lesions. For instance, in clinical settings, a tissue lesion of interest may be efficiently imaged and marked by radiologic markers during diagnostic stage, but these radiologic markers are not visible to surgeons intraoperatively in all surgical scenarios. As another example, fluorescent dye markers have been used widely in biomedical diagnosis and imaging. However, a typical fluorescent dye, such as indocyanine green, still suffers from major limitations for its utilization as a tissue marker in vivo due to its fast clearance, concentration-dependent aggregation, rapid protein binding, and bleaching effect due to various physicochemical attributes. Other difficulties may arise when the detection modality available for a particular clinical procedure is not compatible with the type of tissue being detected. For instance, lung tissue is porous with a high density of air to tissue interfaces, which interfere with ultrasound energy propagation.

Therefore, there remains a continuing need in the art to develop a simplified yet versatile and durable solution to tissue markers that are detectable via multiple detection modalities, retain and preserve the detectability of each marker element in the tissue marker, and persist in the tissues over a suitable time period.

SUMMARY

In at least one aspect, a composite marker may be summarized as comprising: a gel body having an outer surface; a first plurality of ultrasound reflective elements carried in or on the gel body; and at least one radiopaque element (e.g., radiopaque wire, radiopaque band and/or radiopaque clip) carried in or on the gel body. The at least one radiopaque element is advantageously not disposed around the outer surface of the gel body. Each ultrasound reflective element may respectively comprise a body having at least one cavity and at least one fluid (e.g., gas, liquid, or a combination of gas and liquid or vapor) in the at least one cavity to provide reflectivity of ultrasound imaging signals.

The gel body may take the form of a rod, or a roll, for instance a cylindrical roll or a spiral (e.g., volute) roll. The gel body may include a cavity in which a radiopaque element is positioned or located. The cavity of the gel body may be open at one or both ends thereof. Alternatively, the cavity of the gel body may be closed at one or both ends thereof. For example, the gel body may be sized such that one or both ends thereof swell shut when exposed to bodily fluid for a duration of time. Also for example, one or both ends of the gel body may be crimped shut. Additionally or alternatively, a plug (e.g., gel plug) may be positioned in one or both ends of the gel body to close the ends thereof. Additionally or alternatively, an end cap (e.g., gel end cap) may be positioned over one or both ends of the gel body to close the ends thereof.

The gel body may have a first set of physical properties, while another portion of the composite marker, e.g., plug, end cap), may have a second set of physical properties, at least one physical property of the second set of physical properties different that at least one physical property of the first set of physical characteristics. For instance, the gel body and another portion of the composite maker may be made of different materials from one another, have different levels or extensiveness of cross-linking from one another, different rates of hydration and/or associated swelling, and/or different types and/or distributions of ultrasound reflective elements 1102a, 1102c from one another. For instance, the gel body may comprise a gelatin that has been freeze dried, while one or more end caps or plugs may be formed of PEG.

In another aspect, a composite marker may be summarized as comprising: a gel body having an outer surface; an activated and/or hydrolyzed fluorescent dye carried in or on the gel body; and at least one radiopaque element (e.g., radiopaque wire, radiopaque band and/or radiopaque clip) carried in or on the gel body. The at least one radiopaque element is advantageously not disposed around the outer surface of the gel body.

In yet another aspect, a composite marker may be summarized as comprising: a first gel body having an outer surface; at least one radiopaque element (e.g., radiopaque wire or radiopaque band) disposed around and contacting at least a portion of the outer surface of the first gel body, and a second gel body carrying at least one contrast material in or on the second gel body detectable by a detection modality different than X-ray imaging. The second gel body is physically coupled to the first gel body.

In at least one aspect, a method for forming a composite marker may be summarized as comprising: incorporating at least one radiopaque element (e.g., radiopaque wire, radiopaque band, and/or radiopaque clip) to a gel body, and casting the gel body incorporating the at least one radiopaque element to form the composite marker. The method may further comprise, prior to incorporating, mixing a gel or gel forming material with at least one contrast material detectable via a detection modality different than X-ray imaging, to result in a gel body carrying the at least one contrast material in or on the gel body.

In at least one aspect, a method of marking a target site in a mammalian subject may be summarized as comprising: administering parenterally to the target site in the mammalian subject a composite marker comprising: a gel body having an outer surface; a first plurality of ultrasound reflective elements carried in or on the gel body, each ultrasound reflective element respectively comprising a body having at least one cavity and at least one fluid (e.g., gas, liquid, or a combination of gas and liquid or vapor) in the at least one cavity to provide reflectivity of ultrasound imaging signals; and at least one radiopaque element (e.g., radiopaque wire, radiopaque band, and/or radiopaque clip) carried in or on the gel body, wherein the at least one radiopaque element is not disposed around the outer surface of the gel body. The method also comprises detecting the target site and the composite gel marker with ultrasound imaging or X-ray imaging.

In at least one aspect, a method of marking a target site in a mammalian subject may be summarized as comprising: administering parenterally to the mammalian subject a composite marker, comprising: a gel body having an outer surface; an activated and/or hydrolyzed fluorescent dye carried in or on the gel body; and at least one radiopaque element (e.g., radiopaque wire, radiopaque band, and/or radiopaque clip) carried in or on the gel body, wherein the at least one radiopaque element is not disposed around the outer surface of the gel body. The method also comprises detecting the target site and the composite gel marker with X-ray imaging or a detection modality that detects fluorescence.

In at least one aspect, a method of marking a target site in a mammalian subject may be summarized as comprising: administering parenterally to the mammalian subject a composite marker, comprising: a first gel body having an outer surface; at least one radiopaque element (e.g., radiopaque wire, radiopaque band) disposed around and contacting at least a portion of the outer surface of the first gel body, and a second gel body carrying at least one contrast material in or on the second gel body detectable by a detection modality different than X-ray imaging, the second gel body physically coupled to the first gel body. The method also comprises detecting the target site and the composite gel marker with X-ray imaging or a detection modality capable of detecting the at least one contrast material.

Additional aspects, advantages and features of the various embodiments and implementations of the invention(s) are set forth in this specification, and in part will become apparent to those skilled in the art on examination of the following, or may be learned by practice of the invention. The various embodiments and implementations of invention(s) disclosed in this application is not limited to any particular set of or combination of aspects, advantages and features. It is contemplated that various combinations of the stated aspects, advantages and features make up the various embodiments and implementations of the invention(s) disclosed in this application.

BRIEF DESCRIPTION OF THE DRAWINGS

The drawings are intended to illustrate certain exemplary embodiments and are not limiting. In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIG. 2A is a cross-sectional view of an ultrasound reflective element similar in at least some respects to that of FIG. 1B, with the addition of a hydrophobic coating on the ultrasound reflective element, and with the addition of a contrast material located inside the cavity of the ultrasound reflective element according to another illustrated implementation.

FIG. 2B is a cross-sectional view of an ultrasound reflective element similar in at least some respects to that of FIG. 1B, with the addition of a hydrophobic coating on the ultrasound reflective element, and with the addition of a contrast material embedded in the ultrasound reflective element according to another illustrated implementation.

FIG. 2C is a cross-sectional view of an ultrasound reflective element similar in at least some respects to that of FIG. 1C, with the addition of a hydrophobic coating on the ultrasound reflective element, and with the addition of a contrast material inside the cavity of the ultrasound reflective element according to another illustrated implementation.

FIG. 2D is a cross-sectional view of an ultrasound reflective element similar in at least some respects to that of FIG. 1C, with the addition of a hydrophobic coating on the ultrasound reflective element, and with the addition of a contrast material embedded in the ultrasound reflective element according to another illustrated implementation.

FIG. 3 is an enlarged view of a contrast material suitable for use with the various illustrated and/or described implementations, with an optional coating or encapsulation of a shell, according to one illustrated implementation.

FIG. 6A is a side elevational view of a composite marker according to at least one illustrated implementation, showing a portion of a radiopaque element in the form of a radiopaque wire or band wrapped around the outer surface of the gel body of the composite marker.

FIG. 6B is an end elevational view of the composite marker of FIG. 6A showing at least a portion of the radiopaque wire or band embedded in the gel body.

FIG. 7A is a cross-sectional view of a composite marker according to at least one illustrated implementation taken along a section line that passes through a longitudinal axis of the composite marker, showing the gel body of the composite marker taking the form of a hollow tube and a radiopaque element in the form of a radiopaque wire or band located in the hollow interior of the hollow tube, with the ends of the hollow tube optionally sealed.

FIG. 7B is the Q-Q' cross-sectional view of the composite marker of FIG. 7A.

FIG. 9A is a cross-sectional view of a composite marker according to at least one illustrated implementation taken along a section line that passes through a longitudinal axis of the composite marker, showing the composite marker comprising a first gel body having an outer surface, at least one radiopaque element in the form of a radiopaque wire or band disposed around and contacting at least a portion of the outer surface of the first gel body, and a second gel body carrying at least one contrast material in or on the second gel body, the second gel body illustrated as a tube having an inner surface, and physically coupled to the first gel body by at least partially contacting an inner surface of the second gel body with the outer surface of the first gel body and with the radiopaque wire or band.

FIG. 9B is an end elevational view of the composite marker of FIG. 9A.

FIG. 10 is a side elevational view of a composite marker according to at least one illustrated implementation, showing the composite marker comprising a first gel body having an outer surface, at least one radiopaque element in the form of a radiopaque wire or band disposed around and contacting at least a portion of the outer surface of the first gel body, a second gel body carrying at least one contrast material in or on the second gel body, and optionally a third gel body, the second gel body and the optional third gel body illustrated as physically coupled to the first gel body, and in which the optional third gel body optionally carries at least one contrast material in or on the third gel body.

FIG. 11A is a side elevational view showing a portion of a composite marker according to at least one illustrated implementation, and in particular shows a gel body with a first plurality of ultrasound reflective elements dispersed therein, the gel body and ultrasound reflective elements which can be formed as part of manufacturing the composite marker.

FIG. 11B is an end elevational view of the portion of the composite marker of FIG. 11A.

DETAILED DESCRIPTION OF THE EMBODIMENTS

Figure 1A:
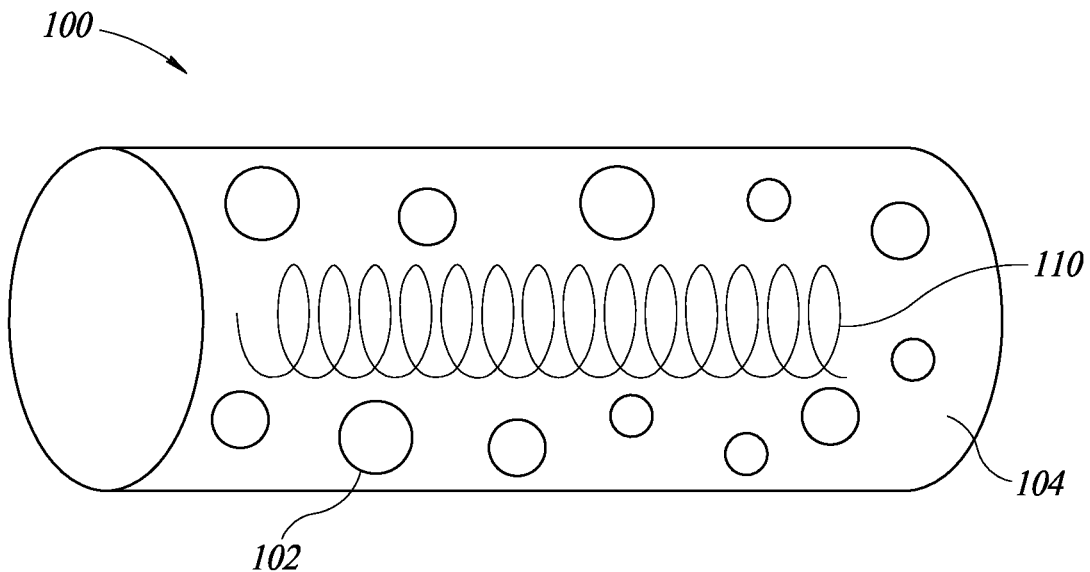
FIG. 1A is an isometric view of a composite marker according to at least one illustrated implementation, showing the composite marker comprising a gel body having an outer surface, a plurality of ultrasound reflective elements, and at least one radiopaque element, illustrated as a radiopaque wire or band, with the ultrasound reflective elements dispersed in the gel body and the at least one radiopaque wire or band disposed in the gel body.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with markers, biopsy devices, and/or medical imaging technology (e.g., ultrasound imagers, MRI imagers, X-ray imagers) have not been shown or described in detail to avoid unnecessarily obscuring descriptions of the embodiments.

Unless the context requires otherwise, throughout the specification and claims which follow, the word "comprise" and variations thereof, such as "comprises" and "comprising" are to be construed in an open-ended, inclusive sense, e.g., as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

The ability to identify, locate, and mark features within the body of a patient has many useful indications. Identifying a specific area within a patient's body with a marker that may be detected at a later time may be useful for a variety of purposes including monitoring that marked area over time, locating a tumor or other type of tissue lesion or abnormality for subsequent study, and performing treatment or surgical procedure such as ablation, adjuvant therapy, or surgical removal. In certain clinical settings, difficulties may arise where a tissue lesion of interest is most efficiently detected and marked using a first detection modality, but surgical removal of the tissue lesion is best accomplished using a second detection modality. In such cases, a marker that persists in the tissue and is stable in position for a period time after deployment and that can be detected by at least two distinct detecting modalities may be useful. Some contrast materials, such as fluorescent dye markers (e.g., indocyanine green), although used widely in biomedical diagnosis and imaging, still suffer from major limitations for its utilization as a tissue marker in vivo. For instance, in the case of indocyanine green, the limitations are due to its fast clearance, concentration-dependent aggregation, rapid protein binding, and bleaching effect due to various physicochemical attributes. In such cases, a marker that can encapsulate the contrast material and "lock" the contrast material in its activated form may be useful. Additionally or alternatively, a marker that can encapsulate the contrast material and hold the contrast material in an un-activated form until inserted into the body and activated (e.g., by hydration from bodily fluid) may be useful.

The structures, articles and methods described herein provide useful solutions to identify, locate, and mark features within the body of a patient for various purposes. Provided here are new composite tissue markers that employ a gel carrier to carry at least one radiopaque element (e.g., radiopaque wire or band or radiopaque clip) and one or more other contrast materials, each detectable by a detection modality different than one another.

A composite marker may comprise: a gel body having an outer surface; a plurality of ultrasound reflective elements carried in or on the gel body; and at least one radiopaque element (e.g., radiopaque wire or band or radiopaque clip) carried in or on the gel body. The at least one radiopaque element (e.g., radiopaque wire or band or radiopaque clip) is not disposed around the outer surface of the gel body, for instance advantageously encapsulating radiopaque element in gel body. Each ultrasound reflective element may respectively comprise a body having at least one cavity (e.g., a shell) and at least one fluid (e.g., gas, liquid, combination of gas and liquid or vapor) in the at least one cavity to provide reflectivity of ultrasound imaging signals.

FIG. 1A shows a composite marker 100 according to at least one illustrated implementation, that can be used to mark a target site in a mammalian subject. As illustrated, the composite marker 100 comprises a plurality of ultrasound reflective elements 102 (only one called out) and at least one radiopaque element, illustrated as a radiopaque wire or band 110 carried in or on the gel body 104. The gel body 104 binds the plurality of ultrasound reflective elements 102 and the at least one radiopaque wire or band 110 together.

As explained herein, the gel body can take any of a variety of forms, for example a natural gelatinous material, a synthetic polymer, or a combination thereof. Suitable materials may, for example include any one or more of: i) a protein selected from the group consisting of collagen, gelatin, fibrin, fibronectin, and albumin; ii) a polysaccharide selected from the group consisting of cellulose or methyl cellulose, hyaluronic acid, chitin, chitosan, and calcium alginate; iii) a synthetic polymer selected from the group consisting of polyvinyl alcohol (PVA), polyglycolic acid (PGA), polylactic acid (PLA), poly(glycolic-co-lactic acid) (PLGA), polycaprolactone (PCL), polymethacrylate (PMA), polymethylmethacrylate (PMMA), polyethylene oxide (PEO), polyamine, polyoxaamide, polyoxaester, polyethylene glycol (PEG), polypropylene (PP), polytetrafluoroethylene (PTFE), polyester, polyetheretherketone (PEEK), and a copolymer thereof; or a mixture of any two or more members from i), ii), or iii). The gel body may in some implementations be at least partially cross-linked, optionally processed by a physical process, a chemical modification, and/or using a crosslinking agent. For instance, the gel body is rendered at least partially cross-linked by using a cross-linking agent selected from the group consisting of an aldehyde, glutaraldehyde, glyceraldehyde, dialdehyde, starch, epoxide, dimethyl adipimidate, glucosepane, carbodiimide, pentosidine, isocyanate or polyisocyanate, metallic cross linker, ionic cross linker, acrylic compound, alginate, sulfhydryl, genipin, and a combination thereof. Alternatively or additionally, the gel body is rendered at least partially cross-linked by freezing and/or thawing.

Ultrasound Reflective Element

The ultrasound reflective element 102 has the structural characteristics to provide reflectivity of ultrasound signals. For instance, each ultrasound reflective element 102 can comprise a body having at least one cavity and at least one fluid in the at least one cavity. The ultrasound reflective element 102 may have irregular surface, for example having a rough outer surface to cause scattering or dispersion of ultrasound energy.

The ultrasound reflective element 102 may take a wide variety of forms. In some embodiments, each ultrasound reflective element 102 is formed of a shell having an outer wall that forms a cavity or a porous particle having more than one cavities.

Figure 1B:
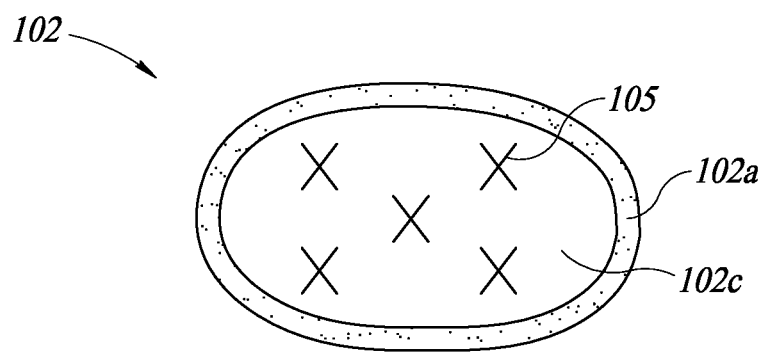
FIG. 1B is a cross-sectional view of an ultrasound reflective element according to at least one illustrated implementation, comprising a body having at least one cavity and at least one fluid in the at least one cavity to provide reflectivity of ultrasound imaging signals, the body illustrated as a shell having an outer wall that forms the cavity.

In at least one implementation, the ultrasound reflective element 102 comprises a shell having an outer wall that forms a cavity. The shell may be a multi-layer hollow shell, for example a shell with an inner layer and an outer layer. FIG. 1B shows an exemplary embodiment of an ultrasound reflective element 102 comprising a body 102a having at least one cavity 102c and at least one fluid 105 in the at least one cavity 102c to provide reflectivity of ultrasound signals. The body 102a is a shell having an outer wall that forms the cavity 102c, the outer wall having an outer surface and an inner surface, the inner surface delineating the interior or cavity 102c.

Figure 1C:
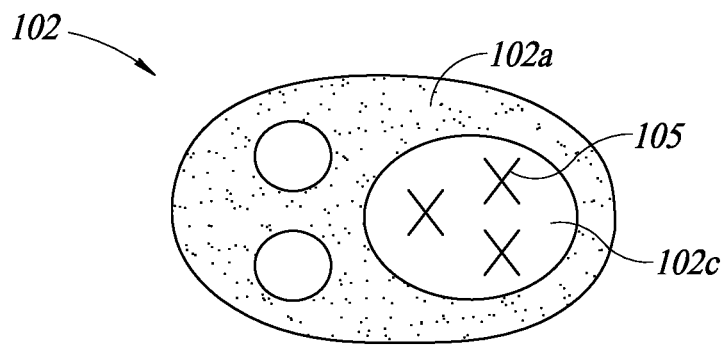
FIG. 1C is a schematic view of an ultrasound reflective element according to at least one illustrated implementation, comprising a body having at least one cavity and at least one fluid in the at least one cavity to provide reflectivity of ultrasound imaging signals, the body illustrated as a porous particle having a plurality of cavities.

In at least one implementation, the ultrasound reflective element 102 is a porous particle having more than one cavities. FIG. 1C shows an exemplary implementation of an ultrasound reflective element 102 comprising a body 102a having cavity plurality of cavities 102c (only one called out) and at least one fluid in the cavities 102c to provide reflectivity of ultrasound signals.

The body 102a of the ultrasound reflective element 102a may have a regular shape or an irregular shape. The body 102a of the ultrasound reflective element 102 may have a spherical shape or a non-spherical shape. In particular, the bodies 102a of two or more ultrasound reflective elements 102a may have the same shape as one another, or the bodies 102a of two or more ultrasound reflective elements 102a may have the different shapes from one another.

The body of the ultrasound reflective element may be made from a variety of inorganic material that may exist in an amorphous (or glass) state or in a crystalline state or in a mixture of amorphous and crystalline forms. Suitable inorganic materials include, but are not limited to, borate, alumina, carbonate, bicarbonate, silica, silicate, aluminosilicate, titanium dioxide, and phosphate. Any of these inorganic materials may be in the form of a monomeric salt or in a polymeric or condensed form. Any of these inorganic materials may be mixed with one or more other inorganic materials. Exemplary inorganic materials are silica and titanium dioxide. In at least some implementations, the body 102a of the ultrasound reflective element 102 comprises a bio-compatible material or bio-compatible materials, that are not generally prone to being rejected or producing an undesired reaction by the body of the subject (e.g., patient).

In at least some implementations, the shell or porous particle of the ultrasound reflective element comprises silica or titanium dioxide. In at least one implementation, the shell or porous particle is silica shell or silica particle.

Various techniques to form shells (such as silica shells) suitable for the ultrasound reflective element may be found, for example in: U.S. Pat. Nos. 8,440,229; 9,220,685; 10,328, 160; U.S. patent application Ser. No. 15/706,446; U.S. patent application Ser. No. 15/559,764; and U.S. patent application Ser. No. 15/946,479; all of which are incorporated herein by reference in their entirety. The techniques to form porous particles suitable for the ultrasound reflective element may be found, for example in U.S. Pat. No. 6,254, 852, which is incorporated herein by reference in its entirety.

The at least one fluid 105 in the at least one cavity of the ultrasound reflective element may be a gas or liquid or a combination of gas and liquid (e.g., a vapor) to provide reflectivity of ultrasound signals. The cavity may entrap the gas or liquid or combination of gas and liquid, and may act as acoustic wave reflectors because of the acoustic differences between the contents of the cavity and the body of the ultrasound reflective element. The entrapped fluid (gas or liquid) may provide a suitable echogenic interface to enhance an ultrasound signal. As described in more detail herein, in at least some implementations, the gas or liquid or combination of gas and liquid may be entrapped in the cavity via a coating or layer that overlies an exterior or outer surface of the body 102a.

Any fluid (gas or liquid, or combination of gas or liquid) that can be present during the process of preparing the ultrasound reflective element may be suitable, although those that provide a good response (e.g., return or reflection) to ultrasound may be preferred over those that do not provide a good response to ultrasound. For instance, the entrapped gas may be an elemental gas or a compound gas such as $O_2$, $H_2$, $CO_2$, an inert gas (e.g., $N_2$, helium, argon, or other noble gases). Exemplary entrapped fluids also include a volatile fluid with a boiling point below a bodily temperature (e.g., below 37° C.), such as a fluorocarbon (such as a perfluorocarbon have less than six carbon atoms, e.g., $CF_4$, $C_2F_6$, $C_3F_8$, $C_4F_{10}$, cyclo-$C_4F_8$, $C_5F_{12}$, cyclo-$C_5F_{10}$, cyclo-$C_4F_7$ (1-trifluoromethyl), 2-(trifluoromethyl)-1,1,1,3,3,3-hexafluoro propane, 2-(trifluoromethyl)-1,1,1,3,3,3,4,4,4-nonafluoro butane, perfluorooctane, perfluoro-2-methylpentane, perfluoro-1,3-dimethylcyclohexane, perfluorodecalin, or perfluoromethyldecalin) that is expected to provide useful ultrasound contrast properties. The entrapped fluid may be a mixture of the aforementioned fluids, e.g., air. Additional examples of suitable liquids may be found in U.S. Pat. No. 5,595,723, which is herein incorporated by reference in its entirety. In at least some implementations, the gas or liquid or combination of gas and liquid comprises a bio-compatible material or bio-compatible materials, that are not generally prone to being rejected or producing an undesired reaction by the body of the subject (e.g., patient).

In an exemplary implementation illustrated in FIG. 1B, the cavity 102c of the shell body 102a or the porous particle body 102a contains a fluid 105 (gas or liquid or combination of gas and liquid). Suitable fluids in the cavity 102c of the ultrasound reflective element 102 have been discussed above.

In at least one implementation, the at least one fluid has a vaporization threshold that a liquid-gas transition of the at least one fluid can be triggered by an acoustic energy. For instance, a physical process of vaporization of the liquid can be induced by the pressure waves of ultrasound that cause superheated liquid nanodroplets to form gas bubbles, which can provide ultrasound imaging contrast. A typical candidate for this acoustic vaporization is fluorocarbon fluid. Suitable fluorocarbon fluids have been discussed above. The acoustic vaporization of the fluid may be induced by high intensity focused ultrasound (HIFU) or by low intensity focused ultrasound (LIFU).

In some implementations, the ultrasound reflective element may additionally comprise one or more layers, the layers which may be made from the same material as the body or from different materials than the body of the ultrasound reflective element.

In at least some implementations, each ultrasound reflective element may be porous. For instance, the ultrasound reflective elements may be porous particles with one or more cavities, for instance as illustrated, in FIG. 1C. When the ultrasound reflective element is a shell as shown, e.g., in FIG. 1B, the body of the shell 102a may be porous. Hence, each ultrasound reflective element may optionally comprise a coating, to at least temporarily seal one or more pores thereof, so that the fluid in the at least one cavity of the ultrasound reflective element is entrapped in the cavities or pores of the ultrasound reflective element. FIGS. 2A, 2B, 2C, and 2D show exemplary implementations of an ultrasound reflective element 102 with an optional coating 106 (e.g., a hydrophobic coating) on the ultrasound reflective element. FIGS. 2A, 2B, 2C, and 2D also show exemplary implementations of the ultrasound reflective elements 102 comprising one or more contrast materials 103a, 103b. In particular, FIG. 2A shows an ultrasound reflective element, similar in at least some respects to that of FIG. 1B, with the addition of a hydrophobic coating 106 on at least an outer surface of the body 102a of the ultrasound reflective element 102, and with the addition of a contrast material 103a located inside the cavity 102c of the ultrasound reflective element 102 according to at least one illustrated implementation. FIG. 2B shows an ultrasound reflective element 102, similar in at least some respects to that of FIG. 1B, with the addition of a hydrophobic coating 106 on at least an outer surface of the body 102a of the ultrasound reflective element, and with the addition of a contrast material 103b embedded in the body 102a of the ultrasound reflective element 102, rather than in the cavity 102c, according to another illustrated implementation. FIG. 2C shows an ultrasound reflective element 102, similar in at least some respects to that of FIG. 1C, with the addition of a hydrophobic coating 106 on at least an outer surface of the body 102a of the ultrasound reflective element 102, and with the addition of a contrast material 103a inside the cavity or pores 102c of the ultrasound reflective element 102, according to another illustrated implementation. FIG. 2D shows an ultrasound reflective element 102, similar in at least some respects to that of FIG. 1C, with the addition of a hydrophobic coating on at least an outer surface of the body 102a of the ultrasound reflective element 102, and with the addition of a contrast material 103b embedded in the body 102a of the ultrasound reflective element 102, rather than in the cavity or pore 102c, according to another illustrated implementation.

The coating 106 may be a natural material such as a protein (e.g., collagen, gelatin, fibrin, fibronectin, or albumin), or a polysaccharide (e.g., cellulose or methyl cellulose, hyaluronic acid, chitin, chitosan, or calcium alginate). The coating may be a synthetic polymer such as polyvinyl alcohol (PVA), polyglycolic acid (PGA), polylactic acid (PLA), poly(glycolic-co-lactic acid) (PLGA), polycaprolactone (PCL), polymethacrylate (PMA), polymethylmethacrylate (PMMA), polyethylene oxide (PEO), polyamine, polyoxaamide, polyoxaester, polyethylene glycol (PEG), polypropylene (PP), polytetrafluoroethylene (PTFE), polyester, polyetheretherketone (PEEK), or a copolymer of any of the aforementioned polymers. The coating 106 may be a mixture of any two or more aforementioned materials.

The coating 106 may optionally be a hydrophobic coating. For instance, the coating may be a mono-, di-, tri-, or tetra-alkoxysilane, including but not limited to, propyltrimethoxysilane, hexyltrimethoxysilane, heptyltrimethoxysilane, octyltrimethoxysilane, nonyltrimethoxysilane, decyltrimethoxysilane, dodecyltrimethoxysilane, tridecyltrimethoxysilane, tetradecyltrimethoxysilane, pentadecyltrimethoxysilane, hexadecyltrimethoxysilane, heptadecyltrimethoxysilane, octadecyltrimethoxysilane, phenyltrimethoxysilane, propyltriethoxysilane, hexyltriethoxysilane, heptyltriethoxysilane, octyltriethoxysilane, nonyltriethoxysilane, decyltriethoxysilane, dodecyltriethoxysilane, tridecyltriethoxysilane, tetradecyltriethoxysilane, pentadecyltriethoxysilane, hexadecyltriethoxysilane, heptadecyltriethoxysilane, octadecyltriethoxysilane, phenyltriethoxysilane, methoxy (triethyleneoxy) propyltrimethoxysilane, 3-(methacryloyloxy) propyltrimethoxysilane, m, p-ethylphenethyltrimethoxysilane, 2-[methoxy (polyethyleneoxy) propyl]-trimethoxysilane, 3-am inopropyltrimethoxysilane, 3-mercaptopropyltrimethoxysilane, 3-isocyanatopropyltriethoxysilane, 3-isocyanatopropyltrimethoxysilane, and glycidoxypropyltrimethoxysilane. In at least one embodiment, the hydrophobic coating takes the form of a hydrophobic polymer, for instance a hydrophobic polymer comprising octyltriethoxysilane.

Methods for coating particles are described by Lachman et al., The Theory and Practice of Industrial Pharmacy (Lea & Febiger, 1986). The techniques for coating particles less than about 100 microns typically include air suspension, coacervation-phase separation, multi-orifice centrifugal, and solvent evaporation.

The ultrasound reflective element 102 can have a distinct signal in ultrasound, such as in Doppler ultrasound imaging. In some implementations, a composite marker 100 comprising such ultrasound reflective elements 102, when administered to a target site in a mammalian subject, can provide significantly less marker migration relative to traditional wire localization. In at least one implementation, the ultrasound reflective elements 102 may be identified intraoperatively with color Doppler ultrasound imaging and B-mode ultrasound imaging in an intraoperative setting.

Under B-mode ultrasound imaging, the ultrasound reflective elements 102 in some composite gel marker implementations described and/or illustrated herein may appear similar to other commercially available ultrasound markers. In some cases, under Doppler mode, the ultrasound reflective elements 102 in some composite gel marker implementations described and/or illustrated herein may generate a robust, highly-colored signal. Therefore, the ultrasound reflective elements 102 may produce a readily identifiable region under Doppler ultrasound, allowing for rapid identification and visualization (e.g., color visualization or representation) with appropriately configured ultrasound machines and transducers. The ultrasound reflective elements 102 may each have a size ranging from about 50 nm to about 20 microns. For instance, the ultrasound reflective elements 102 may range from about 50 nm to about 500 nm, from 50 nm to about 350 nm, from about 100 nm to about 2.2 microns, or from about 200 nm to about 2 microns. The ultrasound reflective elements 102 may each have a larger size that may promote stronger reflective ultrasound signals, ranging from about 1 micron to about 20 microns, e.g., from about 1 micron to about 5 microns, or from about 1.8 microns to about 2.2 microns, but should be sufficiently small enough to be incorporated in a gel body deliverable percutaneously.

In some implementations, a plurality of ultrasound reflective elements 102 are carried in or on the gel body 104, for example in a dispersion therein, for instance in a colloidal dispersion. FIG. 1A shows an exemplary implementation of a composite marker 100 where the plurality of ultrasound reflective elements 102 are carried in or on the gel body 104 in a dispersion therein, for instance in a colloidal dispersion.

Other Contrast Materials

The composite marker 100 may also further comprise one or more contrast materials 103 (not shown in FIG. 1A), each of the contrast materials detectable via a respective detection modality that is different from one another, and different than ultrasound imaging and X-ray imaging. Suitable contrast materials 103 may include a wide variety of materials that can produce a return signal distinct from that of the surrounding tissue and can be detected via a variety of corresponding detection modalities different than ultrasound imaging (detecting the ultrasound reflective elements) and X-ray imaging (detecting the radiopaque wire or band) including but not limited to, visual observation, fluoroscopy, MRI, nuclear-based imaging, and the like.

The contrast material 103 may include two or more different contrast materials, each detectable by a respective detection modality that is different from one another and different from ultrasound imaging and/or different from X-ray imaging.

The contrast material may include, for instance, a visually detectable materials such as a dye or a pigment. Exemplary visually detectable materials are a pigment, a visible dye, a fluorescent dye, a near-infrared dye, and a UV dye. In some implementations, the contrast material includes a cyanine dye selected from the group consisting of a carbocyanine, an oxacarbocyanine, a thiacarbocyanine, and a merocyanine. In some implementations, the contrast material includes at least one of: methylene blue, indigo dye, or indocyanine green. In at least one implementation, the contrast material includes indocyanine green.

The contrast material may include, for instance, a material detectable via magnetic resonance imaging (MRI), such as a paramagnetic, superparamagnetic, ferrimagnetic or ferromagnetic compound, or a compound containing other non-zero spin nuclei than hydrogen. Exemplary MRI-detectable materials are a manganese or manganese-based compound; a gadolinium or gadolinium-based compound (e.g., gadolinium DTPA); and ferrous gluconate, ferrous sulfate, iron oxide, or iron platinum.

The contrast material may include, for instance, a radioactive material, detectable via nuclear-based imaging (e.g., scintigraphy, positron emission tomography, or single-photon emission computed tomography). Exemplary radioactive material are radioiodinated compounds, $^{111}$Indium labelled materials, $^{99m}$Tc labelled compounds (e.g., $^{99m}$TcDTPA, $^{99m}$TcHIDA and $^{99m}$Tc labelled polyphosphonates), and $^{51}$Cr labelled compounds (e.g., $^{51}$CrEDTA).

The optional contrast material 103 may be carried in or on the gel body 104 (FIG. 1A) in a dispersion therein, optionally in a colloidal dispersion. In at least some implementations, the plurality of ultrasound reflective elements 102 and the contrast material 103 are carried in or on the gel body 104 in a dispersion therein, for instance in a colloidal dispersion.

When the contrast material 103 is dispersed in the gel body 104, to prevent the contrast material 103 from effusing out of the gel body 104, the contrast material 103 may further comprise a coating or encapsulation of a shell. FIG. 3 shows an exemplary illustrated implementation of a contrast material 103, with an optional coating or encapsulation of a shell 107 on the outer surface of the contrast material 103. This optional coating or encapsulation of a shell 107 can be formed from a variety of inorganic materials including but not limited to borate, alumina, carbonate, bicarbonate, silica, silicate, aluminosilicate, titanium dioxide, and phosphate. Any of these inorganic materials may be in the form of a monomeric salt or in a polymeric or condensed form. Any of these inorganic materials may be mixed with one or more other inorganic materials. Exemplary inorganic materials are silica and titanium dioxide. In at least one implementation, the contrast material 103 further comprises a silica or titanium dioxide coating or encapsulation of a silica or titanium dioxide shell.

In at least some implementations, the optional contrast material 103 may be carried by the ultrasound reflective elements 102. In at least one implementation, at least one contrast material may be present and may be inside the cavity of the ultrasound reflective element. For instance, as illustrated in FIG. 2A and FIG. 2C, a contrast material 103a, together with a fluid 105, is inside the cavity 102c of the body 102a of the ultrasound reflective element 102. In at least one implementation, at least one contrast material 103 may be present and may be embedded in the body 102a of the ultrasound reflective element 102. For instance, in FIG. 2B and FIG. 2D, a contrast material 103*b* is carried in the body 102*a* of the ultrasound reflective element 102.

When the ultrasound reflective element 102 comprises one or more layers, at least one contrast material 103 is not in the layers of the ultrasound reflective element 102. For instance, when the ultrasound reflective element 102 has an outer layer (i.e., a layer formed on an outer surface of the ultrasound reflective element 102, e.g., an outer silica layer), contrast material 103 is not included in or otherwise omitted from the outer layer of the ultrasound reflective element.

Alternatively, when the ultrasound reflective element 102 comprises one or more layers, at least one contrast material 103 may be located in one or more of the layers of the ultrasound reflective element 102. For instance, when the ultrasound reflective element 102 has an outer layer (i.e., a layer formed on an outer surface of the ultrasound reflective element 102, e.g., an outer silica layer), contrast material 103 may be included in the outer layer of the ultrasound reflective element 102, or alternatively or additionally included in an inner layer of the ultrasound reflective element 102.

In at least one implementation, the optional contrast material can be entrapped in the ultrasound reflective element (e.g., silica shell or silica particle) together with a fluid (e.g., a perfluorocarbon fluid) using single emulsion method.

Radiopaque Element

The at least one radiopaque element 110 carried in or on the gel body 104 comprises a radiopaque material, detectable via X-ray imaging (e.g., computed tomography, fluoroscopy). Suitable radiopaque materials include a radiopaque metal, such as stainless steel, platinum, gold, iridium, titanium, tantalum, tungsten, silver, rhodium, nickel, bismuth, and barium. Suitable radiopaque materials also include an alloy of two or more of the radiopaque metals, an oxide of the radiopaque metal, a sulfate of the radiopaque metal, and a carbonate of the radiopaque metals. Suitable radiopaque materials may also include radiopaque ceramics. A combination of any two or more aforementioned radiopaque materials can be used to form the element.

In at least some implementations, the radiopaque element 110 may take the form of a radiopaque wire or band or a radiopaque clip (e.g., biopsy clip). As used herein and the claims, the term radiopaque clip refers to a radiopaque marker body that can be used to identify a portion of tissue using X-ray imaging, whether or not the radiopaque clip itself can be physically attached to the portion of tissue, in contrast to some other element (e.g., composite marker, gel body) which may physically couple the radiopaque clip to the tissue.

The at least one radiopaque element 110 used as part of the composite marker 100 (FIG. 1) may take any shape available to one skilled in the art. For instance, a radiopaque wire or band may take the form of a straight line, helix, open coil, closed coil, serpentine loop, lemniscate, circle, wavy circle, etc. Also for instance, a radiopaque clip may take the form of a twist, bowtie, dumbbell, T-shape, U-shape, V-shape, W-shape, or nearly any other three-dimensional shape that may produce a distinct image signature when subjected to X-rays from any of a variety of directions.

Figure 4A:
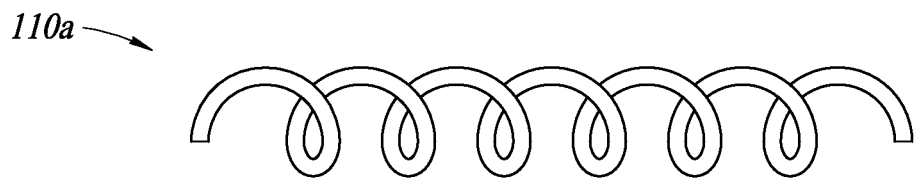
FIG. 4A is side elevational view of a radiopaque element in the form of a radiopaque wire or band according to at least one illustrated implementation, the radiopaque wire or band having a helical shape.
Figure 4B:
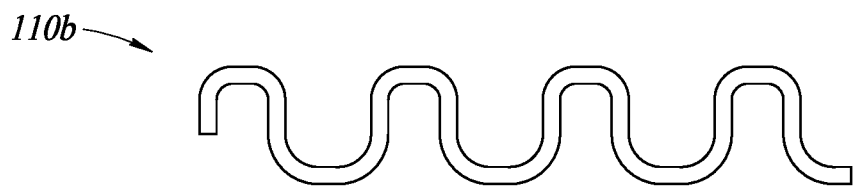
FIG. 4B is side elevational view of a radiopaque element in the form of a radiopaque wire or band according to at least one illustrated implementation, the radiopaque wire or band having a serpentine or and/or convoluted shape.
Figure 4C:
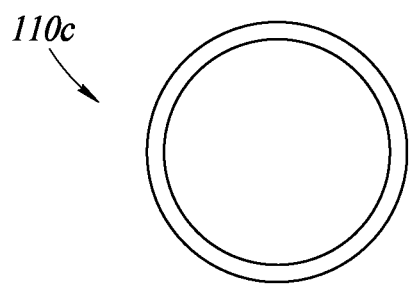
FIG. 4C is an end elevational view of a radiopaque element in the form of a radiopaque wire or band according to at least one illustrated implementation, the radiopaque wire or band having a closed shape, for example an oval or circle shape.
Figure 4D:
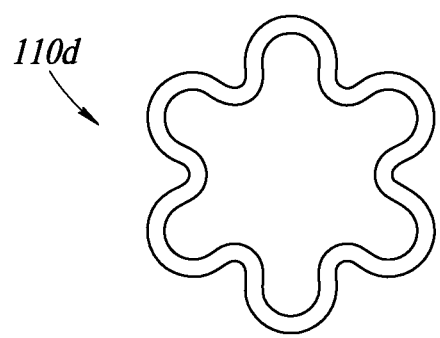
FIG. 4D is an end elevational view of a radiopaque element in the form of a radiopaque wire or band according to at least one illustrated implementation, the radiopaque wire or band having a closed shape, for example a wavy or undulating oval shape or wavy or undulating circle shape.
Figure 4E:
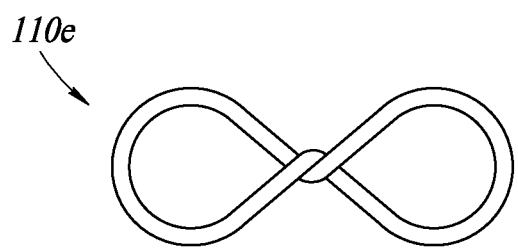
FIG. 4E is an end elevational view of a radiopaque element in the form of a radiopaque wire or band according to at least one illustrated implementation, the radiopaque wire or band having a closed shape, for example a lemniscate shape.

For example, FIG. 4A shows a radiopaque wire or band 110*a* having a helical shape. While illustrated as having relatively widely spaced coils, in at least some implementations the coils of the radiopaque wire or band 110*a* ma be closed spaced together, and even touching adjacent ones of each other. Additionally, a pitch of the coils may differ from that illustrated. In some implementations, the pitch of the coils may change or vary along a length of the radiopaque wire or band 110*a*. FIG. 4B shows a radiopaque wire or band 110*b* having a convoluted or serpentine loop shape. FIG. 4C shows a radiopaque wire or band 110*c* having a closed shape, for example an oval or circular shape. FIG. 4D shows a radiopaque wire or band 110*d* having a closed shape, for example an undulating or wavy oval or circular shape. FIG. 4E shows a radiopaque wire or band 110*c* having a closed shape, for example a lemniscate shape.

The radiopaque wire or band 110*a*-110*e* may have a size (diameter of cross section of wire, or thickness of the band) of about 0.1 mm to about 0.2 mm. For instance, when forming a coil configuration around the outer surface of a gel body 104 having a cross-section diameter of about 1 mm, the coil configuration of the composite marker (having the radiopaque wire or band 110*a*-110*e* wrapping around the outer surface of the gel body 104) can have a coil diameter of about 1.2 to 1.4 mm, which may fit in a 17-gauge needle.

Figure 4F:
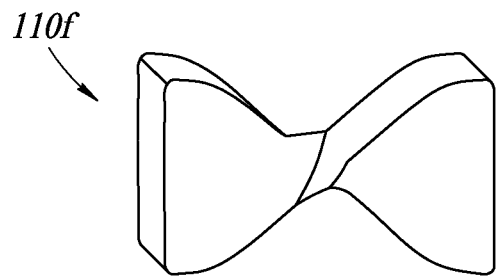
FIG. 4F is a side elevational view of a radiopaque element in the form of a radiopaque clip according to at least one illustrated implementation, the radiopaque clip having a shaped with a pinched neck region, for example having an hour-glass shape, or including a twist and resembling a bowtie.
Figure 4G:
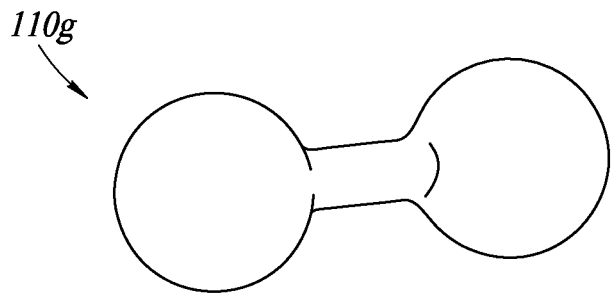
FIG. 4G is a side elevational view of a radiopaque element in the form of a radiopaque clip according to at least one illustrated implementation, the radiopaque clip having opposed bulbous ends, for example resembling a dumbbell.
Figure 4H:
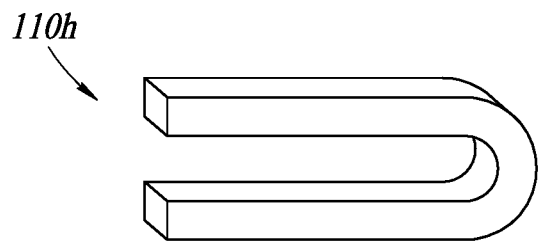
FIG. 4H is a side elevational view of a radiopaque element in the form of a radiopaque clip according to at least one illustrated implementation, the radiopaque clip having opposed legs, for example having a U-shape, V-shape or W-shape.
Figure 4I:
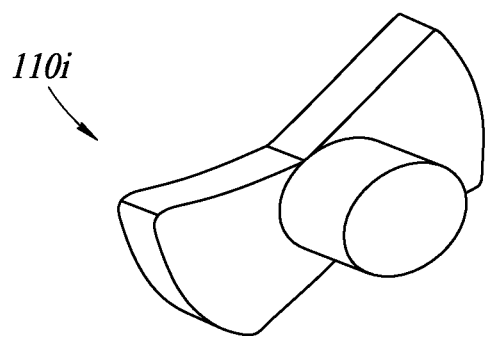
FIG. 4I is an isometric elevational view of a radiopaque element in the form of a radiopaque clip according to at least one illustrated implementation, the radiopaque clip having a T-shape.
Figure 4J:
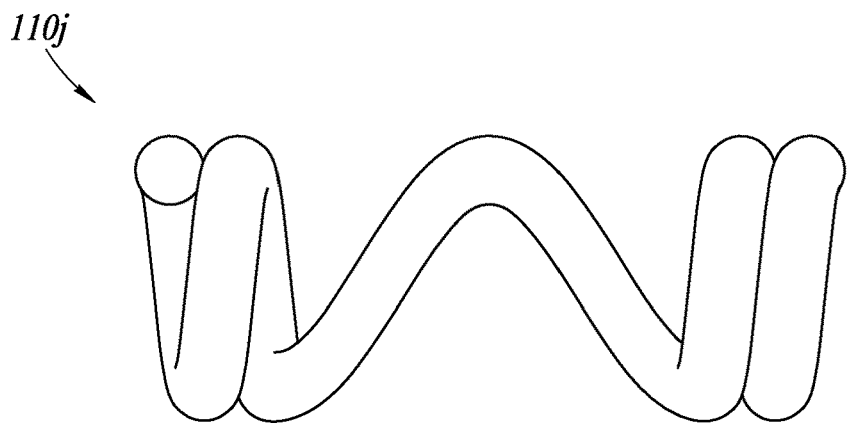
FIG. 4J is side elevational view of a radiopaque element in the form of a radiopaque wire or band according to at least one illustrated implementation, the radiopaque wire or band having a helical shape with a total number of coils per unit of linear distance that is greater proximate opposed ends thereof relative to a total number of coils per unit of linear distance proximate a center thereof.
Figure 4K:
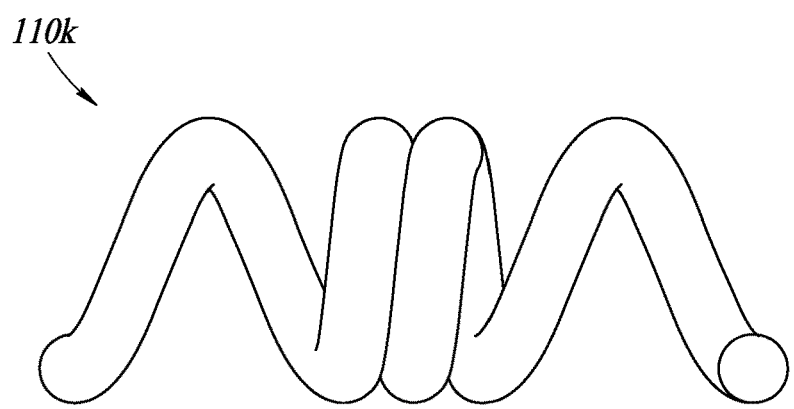
FIG. 4K is side elevational view of a radiopaque element in the form of a radiopaque wire or band according to at least one illustrated implementation, the radiopaque wire or band having a helical shape with a total number of coils per unit of linear distance that is greater proximate a center thereof relative to a total number of coils per unit of linear distance proximate opposed ends thereof.
Figure 4L:
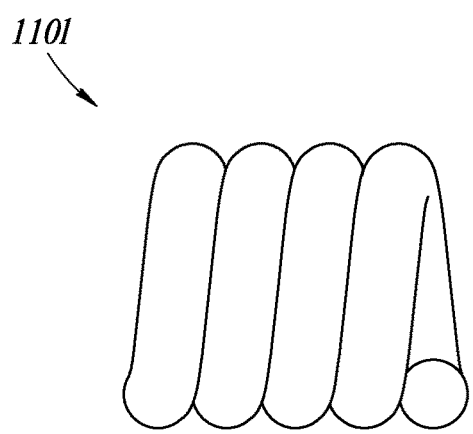
FIG. 4L is side elevational view of a radiopaque element in the form of a radiopaque wire or band according to at least one illustrated implementation, the radiopaque wire or band having a helical shape with a constant total number of coils per unit of linear distance along an entire length thereof, the constant total number of coils per unit of linear distance being relatively high.
Figure 4M:
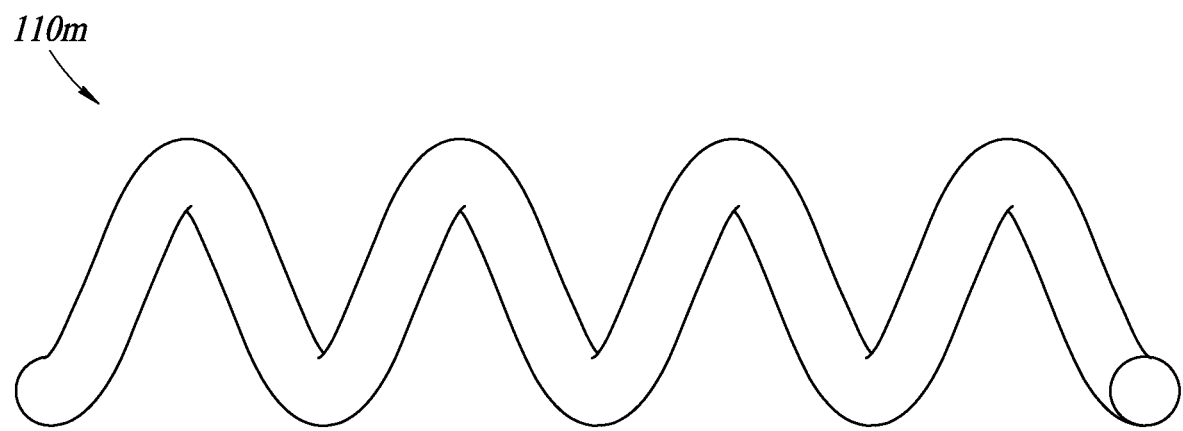
FIG. 4M is side elevational view of a radiopaque element in the form of a radiopaque wire or band according to at least one illustrated implementation, the radiopaque wire or band having a helical shape with a constant total number of coils per unit of linear distance along an entire length thereof, the constant total number of coils per unit of linear distance being relatively low.
Figure 4N:
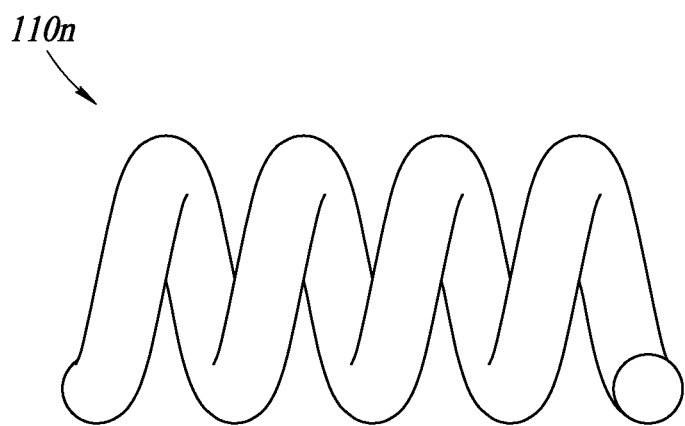
FIG. 4N is side elevational view of a radiopaque element in the form of a radiopaque wire or band according to at least one illustrated implementation, the radiopaque wire or band having a helical shape with a constant total number of coils per unit of linear distance along an entire length thereof, the constant total number of coils per unit of linear distance relatively intermediate in number.

FIG. 4J shows a radiopaque element in the form of a radiopaque wire or band 110*j* according to at least one illustrated implementation, the radiopaque wire or band 110*j* having a helical shape with a total number of coils per unit of linear distance that is greater proximate opposed ends thereof relative to a total number of coils per unit of linear distance proximate a center thereof. The radiopaque wire or band 110*j* has closed ends, an outermost coil at each end contacting a respective inwardly adjacent coil. FIG. 4K shows a radiopaque element in the form of a radiopaque wire or band 110*k* according to at least one illustrated implementation, the radiopaque wire or band 110*k* having a helical shape with a total number of coils per unit of linear distance that is greater proximate a center thereof relative to a total number of coils per unit of linear distance proximate opposed ends thereof. The radiopaque wire or band 110*kj* has open ends, an outermost coil at each end not contacting a respective inwardly adjacent coil. FIG. 4L shows a radiopaque element in the form of a radiopaque wire or band 110*l* according to at least one illustrated implementation, the radiopaque wire or band 110*l* having a helical shape with a constant total number of coils per unit of linear distance along an entire length thereof, the constant total number of coils per unit of linear distance being relatively high or having a relatively tight pitch (e.g., successive coils along the length contacting one another). The radiopaque wire or band 110*l* has closed ends, an outermost coil at each end contacting a respective inwardly adjacent coil. FIG. 4M shows a radiopaque element in the form of a radiopaque wire or band 110*m* according to at least one illustrated implementation, the radiopaque wire or band 110*m* having a helical shape with a constant total number of coils per unit of linear distance along an entire length thereof, the constant total number of coils per unit of linear distance being relatively low or having a relatively loose pitch (e.g., successive coils along the length not contacting and widely spaced from one another). The radiopaque wire or band 110*m* has open ends, an outermost coil at each end not contacting a respective inwardly adjacent coil. FIG. 4N shows a radiopaque element in the form of a radiopaque wire or band 110*n* according to at least one illustrated implementation, the radiopaque wire or band 110*n* having a helical shape with a constant total number of coils per unit of linear distance along an entire length thereof, the constant total number of coils per unit of linear distance relatively intermediate in number or having a relatively intermediate pitch (e.g., successive coils along the length not contacting one another and intermediately spaced from one another). The radiopaque wire or band 110m has open ends, an outermost coil at each end not contacting a respective inwardly adjacent coil.

As example the radiopaque wire or bands 110j-110n may be formed of a biocompatible metal wire, for instance a titanium wire, the metal wire having a radius of approximately 0.003 inches, the helix having an outer diameter of approximately 0.03 inches, and a length of approximately 0.06 inches to 0.12 inches. Using different shapes or configurations may advantageously allow different composite markers to be discerned from one another using various imaging techniques, for instance where tumors, other masses, or suspect tissue have been marked at two or more locations on a portion of a body.

Also for example, FIG. 4F shows a radiopaque clip 110f having a shaped with a pinched neck region, for example having an hour-glass shape, or including a twist and resembling a bowtie. FIG. 4G shows a radiopaque clip 110g in the form of a radiopaque clip having opposed bulbous ends, for example resembling a dumbbell. FIG. 4H shows a radiopaque clip 110h having opposed legs, for example having a U-shape, V-shape or W-shape. FIG. 4I shows a radiopaque clip 110i having a T-shape.

The radiopaque clips 110f-110i may have similar dimensions to those discussed above in reference to radiopaque wires or bands 110a-110e or radiopaque wires or bands 110j-110n.

Gel Body

As previously explained, the composite marker 100 includes a gel body 104, which may comprise a natural gelatinous material, a synthetic polymer, or a combination thereof. Suitable natural gelatinous materials include a protein (e.g., collagen, gelatin, fibrin, fibronectin, and albumin), and a polysaccharide (e.g., cellulose or methyl cellulose, hyaluronic acid, chitin, chitosan, and calcium alginate). Suitable synthetic polymers include polyvinyl alcohol (PVA), polyglycolic acid (PGA), polylactic acid (PLA), poly(glycolic-co-lactic acid) (PLGA), polycaprolactone (PCL), polymethacrylate (PMA), polymethylmethacrylate (PMMA), polyethylene oxide (PEO), polyamine, polyoxaamide, polyoxaester, polyethylene glycol (PEG), polypropylene (PP), polytetrafluoroethylene (PTFE), polyester, polyetheretherketone (PEEK), and a copolymer of any of the aforementioned polymers. A mixture of any two or more materials selected from any aforementioned natural gelatinous materials and synthetic polymers can be used as the gel body. In at least one embodiment, the gel body comprises a natural collagen or gelatin. In at least one embodiment, the gel body comprises a synthetic PVA or PEG.

The gel body 104 may degrade in vivo in the tissues of a host mammalian subject within of a short period of time (a few weeks to a few months) or may persist in the tissues of a host mammalian subject over a long period of time (e.g., 60 years or longer). The gel body may be at least partially cross-linked to decrease the rate of degradation and to persist in the tissues of the host mammalian subject for a prolonged period of time, for instance, over a period of hours, days, a week or weeks, a month or months, or even for a year or years. When degradable, the rate of degradation of the composite marker in the tissues of a host mammalian subject may be controlled by the degree of crosslinking of the gel body. The biological degradation takes place at a slower rate as the degree of crosslinking increases.

In some implementations, the gel body may have at least partially degraded over a period of time, exposing at least some or a portion of the ultrasound reflective elements, the radiopaque elements (e.g., radiopaque wire or band or radiopaque clip), or the contrast materials (if present), carried in or on the gel body, to the bodily tissues. These exposed marker elements may degrade in vivo in the tissues of a host mammalian subject within of a short period of time (a few weeks to a few months) or may persist in the tissues of a host mammalian subject over a long period of time (e.g., 60 years or longer).

In some implementations, the degree of crosslinking of the gel body is determined by the desired or defined rate of degradation of the composite marker in the tissues of a host mammalian subject. In at least one implementation, the rate of degradation is such that the composite marker persists in the tissues of the host mammalian subject for a period of at least three weeks, at least four weeks, at least three months, at least six months, or at least nine months.

The crosslinking or partial crosslinking of the gel body may be achieved by a physical process or a chemical modification (with or without using a crosslinking agent). Suitable physical processes are those known to one skilled in the art, including but not limited to, drying (e.g., freeze-drying, critical point drying, or air drying), thermo-dehydration, and radiation (e.g., UV radiation or γ-ray radiation). Suitable chemical modifications are those known to one skilled in the art, including but not limited to, liquid phase crosslinking (e.g., the gel is immersed in a solution of a crosslinking agent to react, and the unreacted crosslinking agent is washed off), vapor phase crosslinking (e.g., the crosslinking reaction of the gel is performed under the vapor of the crosslinking agent, and the unreacted crosslinking agent is flushed off with an air flow), and supercritical fluid crosslinking (e.g., the gel is contacted with a supercritical fluid containing a crosslinking agent to react).

In at least one implementation, the gel body is rendered at least partially cross-linked by freezing and/or thawing.

In at least one implementation, the gel body is rendered at least partially cross-linked by using a crosslinking agent. Suitable crosslinking agents are those known to one skilled in the art for use in crosslinking of polymers, including but not limited to, an aldehyde (e.g., formaldehyde), glutaraldehyde, glyceraldehyde, dialdehyde, starch, epoxide, dimethyl adipimidate, glucosepane, carbodiimide, pentosidine, isocyanate or polyisocyanate, metallic cross-linker, ionic cross-linker, acrylic compound, alginate, sulfhydryl, genipin, and a combination thereof.

The degree of crosslinking of the gel body may be tailored by altering the crosslinking processing duration (for a physical process), the crosslinking reaction time (for a chemical process), the concentration of the crosslinking agent (for a chemical process), the operating temperature or pressure, and other process parameters or reaction conditions.

The gel body may be prepared from a gel or gel forming material. For instance, a dry gel or gel forming material may be mixed with distilled water in a variety of concentrations to tailor the resulting properties to a particular indication or use, for example, in a concentration of about 1 wt % 1 g gel or gel forming material per 100 ml distilled water) to about 50 wt %, such as about 1 wt % to about 10 wt %, about 4 wt % to about 10 wt %, or about 4 wt % to about 6 wt %.

In at least some implementations, a composite marker may comprise: a gel body having an outer surface; an activated and/or hydrolyzed fluorescent dye carried in or on the gel body; and at least one radiopaque element (e.g., radiopaque wire or band or radiopaque clip) carried in or on the gel body. The fluorescent dye may provide a visual detection modality. The detection modality provided by the dye may, for example, be in addition to ultrasound detection and/or X-ray detection modalities. In at least some implementations, the at least one radiopaque element is not disposed around the outer surface of the gel body.

Figure 5A:
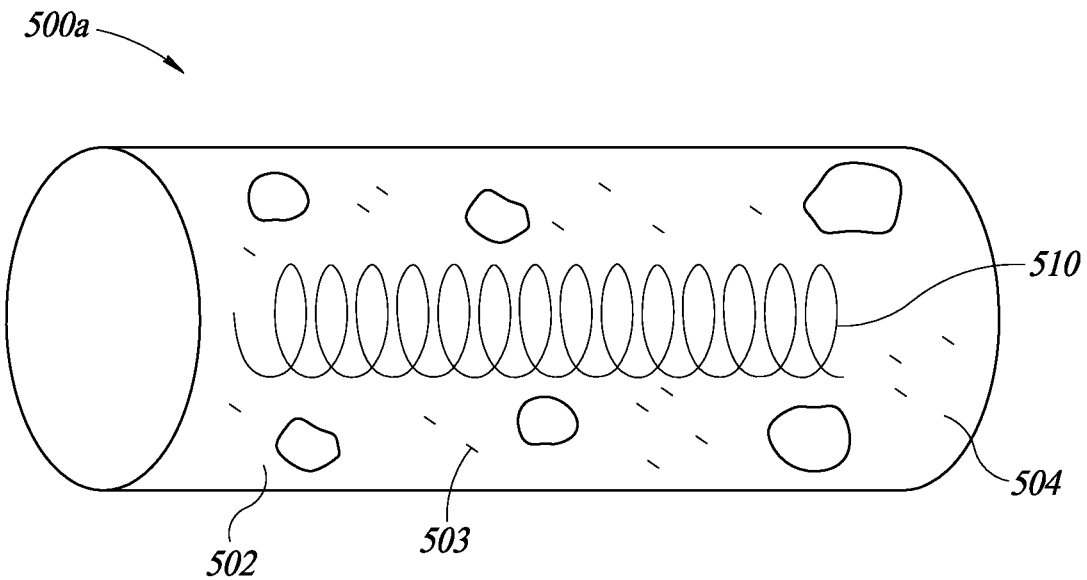
FIG. 5A is an isomeric view of a composite marker according to at least one illustrated implementation, showing the composite marker comprising a gel body having an outer surface, an activated and/or hydrolyzed fluorescent dye, at least one radiopaque element in the form of a radiopaque wire or band, and optionally, one or more other contrast materials, with the activated and/or hydrolyzed fluorescent dye and optionally other contrast materials dispersed in the gel carrier, and the at least one radiopaque wire or band illustrated as disposed in the gel body.

FIG. 5A shows an exemplary implementation of a composite marker 500a that can be used to mark a target site in a mammalian subject. In at least one implementation, the composite marker 500a comprises an activated and/or hydrolyzed fluorescent dye 503 and at least one radiopaque element, illustrated as a radiopaque wire or band 510, carried in or on the gel body 504. The gel body 504 binds the activated and/or hydrolyzed fluorescent dye 503 and the at least one radiopaque element together.

Fluorescent Dye

The activated and/or hydrolyzed fluorescent dye 503 may be formed by activating and/or hydrolyzing a fluorescent dye when exposing the fluorescent dye to the gel body when forming the composite marker. The phrase "activated and/or hydrolyzed fluorescent dye" refers to a form of a fluorescent dye molecule that is formed when exposing the fluorescent dye material to the gel body to prepare the composite marker, during which process the fluorescent dye molecule is activated and/or hydrolyzed so that it can emit fluorescence. By forming a composite marker using a gel body, the fluorescent dye molecule is "locked" (or at least prolonged) in its activated and/or hydrolyzed form so that the photobleaching effect may be minimized. Taking ICG as an example, in aqueous solution, ICG has the maximum absorption at 780 nm and a relatively low quantum yield for fluorescence. Nevertheless, free form of ICG can be rapidly cleared from the blood stream and photobleaching. When incorporating ICG into the gel body to form the composite marker, ICG is exposed to the water component in the gel body to be activated and/or hydrolyzed, which may provide a same or similar absorption signature as ICG in solution. Moreover, incorporating the activated and/or hydrolyzed ICG in the composite marker may decrease the bleaching effect of the ICG dye and increase the effective length of time in which the ICG dye can be detected and monitored.

Suitable fluorescent dyes include, but are not limited to, a cyanine dye, such as a carbocyanine, an oxacarbocyanine, a thiacarbocyanine, and a merocyanine. An exemplary cyanine dye is indocyanine green.

The activated and/or hydrolyzed fluorescent dye 503 may be carried in or on the gel body 504 in a dispersion therein, for instance in a colloidal dispersion. FIG. 5A shows an exemplary implementation of a composite marker 500a where the activated and/or hydrolyzed fluorescent dye 503 is carried in or on the gel body 504 in a dispersion therein, for instance in a colloidal dispersion.

When the fluorescent dye is dispersed in the gel body, to prevent the activated and/or hydrolyzed fluorescent dye from effusing out of the gel body, the activated and/or hydrolyzed fluorescent dye may further comprise a coating or encapsulation of a shell. This coating or encapsulation of a shell can be formed from a variety of inorganic material including but not limited to borate, alumina, carbonate, bicarbonate, silica, silicate, aluminosilicate, titanium dioxide, and phosphate. Any of these inorganic materials may be in the form of a monomeric salt or in a polymeric or condensed form. Any of these inorganic materials may be mixed with one or more other inorganic materials. Exemplary inorganic materials are silica and titanium dioxide. In at least one implementation, the activated and/or hydrolyzed fluorescent dye further comprises a silica or titanium dioxide coating or encapsulation of a silica or titanium dioxide shell.

The composite marker 500a may also further comprise one or more contrast materials 502. The contrast material 502 may include two or more different contrast materials, each detectable by a respective detection modality that is different from one another and different than detection of fluorescence and X-ray imaging.

In some implementations, the optional contrast material 502 comprises a plurality of ultrasound reflective elements 102 each respectively comprising a body having at least one cavity and at least one fluid in the at least one cavity to provide reflectivity of ultrasound imaging signals. In some implementations, the contrast material 502 comprises a plurality of ultrasound reflective elements 102 each respectively comprising a body having at least one cavity and at least one fluid 105 in the at least one cavity to provide reflectivity of ultrasound imaging signals.

In these activated and/or hydrolyzed fluorescent dye implementations, all above descriptions and implementations relating to the ultrasound reflective elements 102, including the variety of forms that the ultrasound reflective elements 102 may take, the shape and materials of the body of the ultrasound reflective elements 102a, the techniques to form the ultrasound reflective elements, the fluid 105 entrapped in the cavity or pores of the ultrasound reflective elements, the coating 106 on the ultrasound reflective elements, the sizes of the ultrasound reflective elements, and the exemplary implementations illustrated in FIGS. 1B-1C and FIGS. 2A-2D, are all applicable to the implementation(s) relating to the optional contrast material 502 in the composite marker 500a.

In some implementations, the optional contrast material 502 comprises a plurality of ultrasound reflective elements 102, each being formed of a shell 102a having an outer wall that forms a cavity 102c or a porous particle 102a having one or more cavities 102c or pores (as shown in FIGS. 1B and 1C). In some implementations, the shell or porous particle comprises silica or titanium dioxide. In at least one implementation, the shell or porous particle is silica shell or silica particle.

In some implementations, the optional contrast material 502 comprises a plurality of ultrasound reflective elements 102, each respectively comprising a body having at least one cavity containing entrapped fluid (e.g., gas or liquid or combination of gas and fluid or vapor) 105 to provide reflectivity of ultrasound imaging signals. In at least one implementation, the at least one fluid has a vaporization threshold that a liquid-gas transition of the at least one fluid can be triggered by an acoustic energy. The acoustic vaporization of the fluid may be induced by high intensity focused ultrasound (HIFU) or by low intensity focused ultrasound (LIFU).

In some implementations, the optional contrast material 502 comprises a material visually detectable in a detection modality other than detection of fluorescence, such as a dye or a pigment, that is not a fluorescent dye. Exemplary visually detectable materials are a pigment, a visible dye, and a UV dye. In at least one embodiment, the at least one contrast material includes at least one of: methylene blue and indigo dye.

In some implementations, the optional contrast material 502 comprises a material detectable via magnetic resonance imaging (MRI). Suitable MRI-detectable materials have been discussed above relating to the contrast material 103.

In some implementations, the optional contrast material 502 comprises a radioactive material, detectable via nuclear-based imaging (e.g., scintigraphy, positron emission tomography, or single-photon emission computed tomography). Suitable radioactive materials have been discussed above relating to the contrast material 103.

In some implementations, the optional contrast material 502 and the activated and/or hydrolyzed fluorescent dye 503 are carried in or on the gel body 504 in a dispersion therein, optionally in a colloidal dispersion. FIG. 5A shows an exemplary implementation of a composite marker 500a where the optional contrast material 502 and the activated and/or hydrolyzed fluorescent dye 503 are carried in or on the gel body 504 in a dispersion therein, for instance in a colloidal dispersion.

When the optional contrast material is dispersed in the gel body, the contrast material may also further comprise a coating or encapsulation of a shell, to prevent the contrast material from effusing out of the gel body. The coating or encapsulation of a shell can be formed from a variety of inorganic materials. Suitable inorganic materials have been discussed above relating to the contrast material 103 and the optional coating or encapsulation of a shell 107.

Figure 5B:
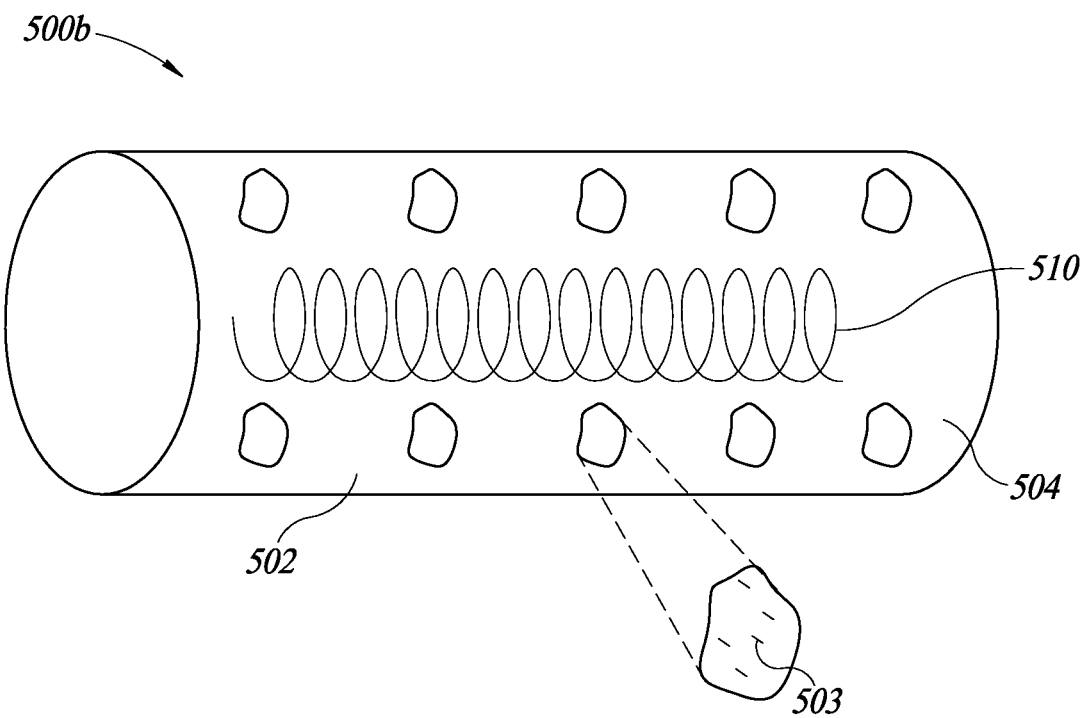
FIG. 5B is an isomeric view of a composite marker according to at least one illustrated implementation, showing the composite marker comprising a gel body having an outer surface, an activated and/or hydrolyzed fluorescent dye, at least one radiopaque element in the form of a radiopaque wire or band, and one or more other contrast materials, with the one or more other contrast materials dispersed in the gel body, and the at least one radiopaque wire or band illustrated disposed in the gel body. An enlarged view shows the activated and/or hydrolyzed fluorescent dye embedded in the one or more other contrast material.

In some implementations, the activated and/or hydrolyzed fluorescent dye may be carried on or embedded in the contrast material 502. For instance, in FIG. 5B, a composite marker 500b includes an activated and/or hydrolyzed fluorescent dye 503 carried on or embedded in the contrast material 502.

In at least one implementation, the optional contrast material 502 comprises a plurality of ultrasound reflective elements 102, each respectively comprising a body having at least one cavity containing entrapped fluid (e.g., gas or liquid or combination of gas and liquid) 105 to provide reflectivity of ultrasound imaging signals; and the activated and/or hydrolyzed fluorescent dye may be carried on or embedded in the contrast material 502. For instance, in FIG. 5B, the activated and/or hydrolyzed fluorescent dye 503, is carried on or embedded in the ultrasound reflective element 502 (or 102). In this implementation, the activated and/or hydrolyzed fluorescent dye may be inside the cavity of the ultrasound reflective element and/or embedded in the body of the ultrasound reflective element, similar to the exemplary implementations illustrated in FIGS. 2A-2D.

In at least one implementation, the activated and/or hydrolyzed fluorescent dye, such as ICG, can be entrapped in the ultrasound reflective element (e.g., silica shell or silica particle) together with a fluid (e.g., a perfluorocarbon fluid) using single emulsion method.

The composite marker 500a, 500b also comprises at least one radiopaque element, in this instance illustrated as a radiopaque wire or band 510 carried in or on the gel body 504, which comprises a radiopaque material, detectable via X-ray imaging (e.g., computed tomography, fluoroscopy).

All above descriptions and implementations discussed and/or illustrated relating to the at least one radiopaque element (e.g., radiopaque wire or band or radiopaque clip) 110, including suitable radiopaque materials for the at least one radiopaque element, and the form, shape, and size of the at least one radiopaque element, are all applicable to the implementation(s) relating to the at least one radiopaque element 510 in the composite marker 500a, 500b.

The composite marker 500a, 500b also comprises a gel body 504, which may comprise a natural gelatinous material, a synthetic polymer, or a combination thereof.

All above descriptions and implementations discussed and/or illustrated relating to the gel body 104, including suitable materials for the gel body, crosslinking of the gel body, the form and size of the gel body, and the preparation of the gel body, are all applicable to the implementation(s) relating to the gel body 504 in the composite marker 500a, 500b.

The gel body 104 or 504 in respective composite marker 100 or 500a, 500b may take a variety of forms, for example depending on a mold or mandrel used when molding or forming the gel body, as well as the particular construction techniques employed to construct or fabricate the composite markers.

In some implementations, the gel body 104 or 504 may take the form of an elongated structure, for example a "solid" rod or a hollow rod or partially hollow rod. As used herein, the term "solid rod" refers to a rod that does not include a longitudinal passage extending entirely or partially therethrough, the term "solid rod" having no bearing on the consistency of the gel body 104 or 504. Thus, a "solid rod" while having no longitudinal passage, may in fact be soft to the touch, for instance a non-cross-linked or lightly cross-linked gel rod. As used herein, the term "hollow rod" refers to a rod that does include a longitudinal passage extending entirely therethrough, and the term "partially hollow rod" refers to a rod that does include a longitudinal passage extending only partially therethrough. Hollow and partially hollow rods may fall in the class of tubes or tubular structures, each having a longitudinal passage extending at least partially therethrough.

In some implementations, the gel body 104 or 504 may take the form of a roll, layered roll, volute, or spiral roll. For example, one or more sheets of gel material may, for instance, be rolled about a mandrel to form a roll, the mandrel removed after forming the roll. Opposed ends of the sheet(s) of gel material may be drawing relatively together to form a closed structure or an open structure with a gap between the opposed ends. Also for example, one or more sheets of gel material may, for instance, be rolled with an increasing or decreasing radius to form a layered roll, volute (e.g., involute) or roll with a spiral profile. Rolls, layered rolls, volutes and/or spiral rolls may fall in the class of tubes or tubular structures, each having a longitudinal passage extending at least partially therethrough.

The term "tube" or tubular as used here refers to an elongated profile that has a hollow cross section (e.g., longitudinal passage extending at least partially therethrough). The term "tubular mold" as used here refers to a mold or mandrel used to produce an item (e.g., gel body) having an elongated profile that has a hollow cross section (e.g., longitudinal passage extending at least partially therethrough). The shape of outer perimeter or outer profile and/or the inner perimeter or inner profile of the cross section of the tube, tubular structure, or tubular mold can take any form or shape, for example: circular, hexagonal, octagonal, triangle, square, rectangular, oval, or elliptical. The outer perimeter or outer profile and the inner perimeter or inner profile may have the same shapes as one another or different shapes from one another For instance, the gel body 104 or 504 may take the form of a rod. FIG. 6A shows an exemplary implementation of a composite marker 100 or 500a, 500b, having a gel body 604 taking the form of a rod. The shape of the rod can be adjusted and controlled by the shape of the mold used when molding the gel body. For instance, a tubular mold having an inner cylindrical or cuboid cavity can mold the gel body into a cylindrical or cuboid rod, respectively. The rod may, for example be a "solid rod", that is a rod having no longitudinal passage.

Typically, when the composite marker comprises only one gel body, the at least one radiopaque element (e.g., radiopaque wire or band or radiopaque clip) is not entirely disposed around the outer surface of the gel body. Instead one portion of the at least one radiopaque element may be wrapped around the outer surface of the gel body, with at least another portion of the radiopaque element embedded in the gel body. FIGS. 6A and 6B show an exemplary implementation of a composite marker 100 or 500a, 500b, having a gel body 604 carrying at least one radiopaque element, illustrated as a radiopaque wire or band 610. The contrast material (ultrasound reflective element 102, or fluorescent dye 503, or other type of contrast material) carried in or on the gel body is not labeled. FIGS. 6A and 6B illustrate one portion of the radiopaque wire or band 610 wrapped around the outer surface of the gel body 604, with another portion of the radiopaque wire or band 610 embedded in the gel body 604.

As noted above, the gel body 104 or 504 may take the form of a tube. FIG. 7B shows an exemplary implementation of a composite marker 100 or 500a, 500b, having a gel body 704 taking the form of a tube. The shape of the tube can be adjusted and controlled by the shape of the mold or mandrel used when molding or otherwise forming the gel body.

In at least some implementations, the radiopaque element (e.g., radiopaque wire or band or radiopaque clip) may positioned, located or otherwise reside in a hollow interior or passage (e.g., longitudinal passage) of the tube. One end or both ends of the tube may be left open. Alternatively, one end or both ends of the tube may be at least partially sealed, for instance with a gel plug or gel forming material, or by being crimped, squeezed or pinched shut. The gel plug or gel forming material may be the same material or different material than the gel material that forms the gel body. The gel plug may be coupled to the gel body via a friction fit, via chemical attraction of via a fusion between the materials. The gel plug may have an outer perimeter designed to be closely received by an inner perimeter of the gel body. The outer perimeter may taper or alternatively flare from one end to the other, the taper or flare matching a complementary flare or taper of the inner perimeter of the gel body.

FIGS. 7A and 7B show an exemplary implementation of a composite marker 100 or 500a, 500b, having a gel body 704 carrying at least one radiopaque element, illustrated as a radiopaque wire or band 710. The contrast material (ultrasound reflective element 102, or fluorescent dye 503, or other type of contrast material) carried in or on the gel body is not labeled. FIGS. 7A and 7B illustrate that the gel body 704 takes the form of a tube having two ends, and the radiopaque wire or band 710 is positioned, located or resides in the hollow interior 707 of the tube 704. FIG. 7A also illustrates an option where one end or both ends of the tube 704 may be at least partially sealed with a gel 714. The gel 714 may be the same material or different material than the material of the gel body 704. Suitable gel or gel forming materials have been discussed above relating to the gel body 104.

Figure 8A:
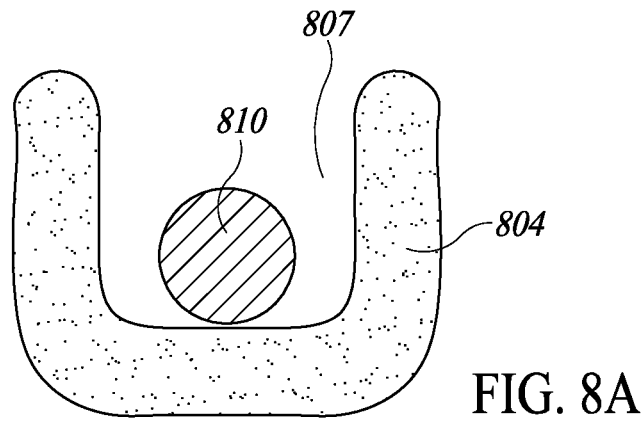
FIG. 8A is an elevational end view of a composite marker according to at least one illustrated implementation, showing a gel body of the composite marker taking the form of an open roll with a radiopaque element in the form of a radiopaque wire or band positioned in an interior cavity of the roll.
Figure 8B:
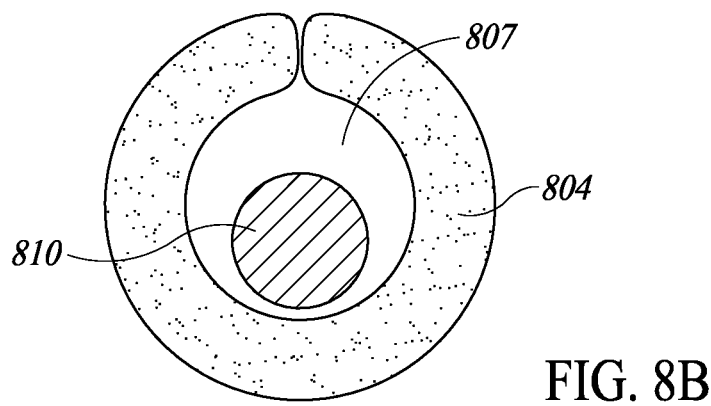
FIG. 8B is an elevational end view of a composite marker according to at least one illustrated implementation, showing a gel body of the composite marker taking the form of a closed or partially closed roll with a radiopaque element in the form of a radiopaque wire or band positioned in an interior cavity of the roll.
Figure 8C:
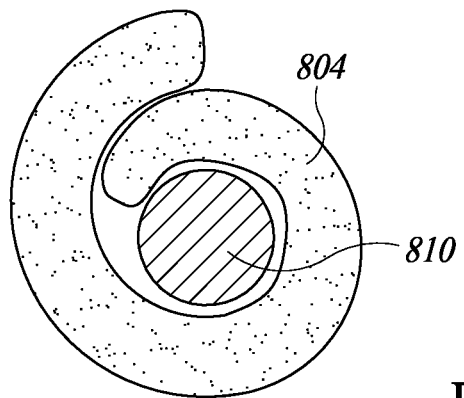
FIG. 8C is an elevational end view of a composite marker according to at least one illustrated implementation, showing a gel body of the composite marker taking the form of a closed and layered or volute or spiral roll with a radiopaque element in the form of a radiopaque wire or band positioned in an interior cavity of the roll.

As noted, the gel body 104 or 504 may take the form of a roll, layered roll, volute or spiral roll. The roll may be partially open (e.g., C-shaped cross-section or profile) or closed (e.g., O-shaped, O-shaped, D-shaped cross-section or profile) a long a longitudinal axis thereof leaving a cavity or passage. The cavity or passage has a pair of ends opposed to one another across a length of the gel body. As described herein, the cavity or passage may be open at one end or open at both ends, or the cavity or passage may be closed at one end or closed at both ends. For instance, one or both ends may be crimped closed, hydrated and swollen closed, plugged closed by a plug and/or capped by an end cap. The radiopaque element (e.g., radiopaque wire or band, radiopaque clip) may be positioned located or otherwise resides in the interior cavity or passage 807 of the roll, layered roll, volute, or spiral roll. FIG. 8A-8C show exemplary implementations of a composite marker 100 or 500a, 500b, having a gel body 804 carrying at least one radiopaque element (e.g., radiopaque wire or band, radiopaque clip) 810. The contrast material (ultrasound reflective element 102, or fluorescent dye 503, or other type of contrast material) carried in or on the gel body is not labeled. FIG. 8A illustrates that the gel body 804 takes the form of an open roll with the radiopaque element 810 positioned or locate or residing in the interior cavity of the gel body 804. FIG. 8B illustrates that the gel body 804 takes the form of a partially closed or closed roll with the radiopaque element 810 in the interior cavity of the roll 804. FIG. 8C illustrates that the gel body 804 takes the form of a closed and layered roll, volute or spiral roll with the radiopaque element 810 in the interior cavity of the gel body 804.

A composite marker may comprise: a first gel body having an outer surface; at least one radiopaque element (e.g., radiopaque wire or band or radiopaque clip) disposed around and contacting at least a portion of the outer surface of the first gel body, and a second gel body carrying at least one contrast material in or on the second gel body detectable by a detection modality different than X-ray imaging. The second gel body is physically coupled to the first gel body.

In some implementations, the first gel body has an outer surface and the at least one radiopaque element (e.g., radiopaque wire or band or radiopaque clip) is disposed around and contacts at least a portion of the outer surface of the first gel body. The second gel body takes the form of a tube having an inner surface, the outer surface of the first gel body is at least in partial contact with the inner surface of the second gel body, and the radiopaque element (e.g., radiopaque wire or band or radiopaque clip) contacts at least a portion of the inner surface of the second gel body.

FIGS. 9A and 9B show an exemplary implementation of a composite marker 900 that can be used to mark a target site in a mammalian subject. In at least one implementation, the composite marker 900 comprises a first gel body 904a having an outer surface, at least one radiopaque element, illustrated as a radiopaque wire or band 910, disposed around and contacting at least a portion of the outer surface of the first gel body 904a, and a second gel body 904b carrying at least one contrast material 903 in or on the second gel body 904b detectable by a detection modality different than X-ray imaging. The second gel body 904b takes the form of a tube having an inner surface, and is physically coupled to the first gel body 904a by having the inner surface of the second gel body 904b at least in partial contact with the outer surface of the first gel body 904a. The radiopaque wire or band 910 contacts at least a portion of the inner surface of the second gel body 904b. The second gel body 904b binds the at least one contrast material 903 and the at least one radiopaque element (e.g., wire or band 910) together.

In some implementations, the first gel body has an outer surface and the at least one radiopaque element (e.g., radiopaque wire or band or radiopaque clip) is disposed around and contacts at least a portion of the outer surface of the first gel body. The second gel body can take any form. For instance, the second gel body may take the form of a rod, a roll or layered roll, volute or spiral roll, or a tube. One end of the second gel body is physically coupled to one end of the first gel body.

In some implementations, the composite marker may further comprises one or more additional gel bodies, in addition to the first and the second gel bodies. Each of the one or more additional gel bodies may optionally carry at least one contrast material in or on the respective additional gel body, detectable via a detection modality that is different from one another, different from the second gel body, and different than X-ray imaging. Each of the additional gel bodies can take any form. For instance, each of the additional gel bodies may take the form of a rod, a roll or layered roll, or volute or spiral roll, or a tube. Each of the additional gel bodies is physically coupled to the first gel body, the second gel body, or a different additional gel body.

FIG. 10 show an exemplary implementation of a composite marker 1000 that can be used to mark a target site in a mammalian subject. In at least one implementation, the composite marker 1000 comprises a first gel body 1004a having an outer surface, at least one radiopaque element, illustrated as a radiopaque wire or band 1010, disposed around and contacting at least a portion of the outer surface of the first gel body 1004a, and a second gel body 1004b carrying at least one contrast material 1003 in or on the second gel body 1004b detectable by a detection modality different than X-ray imaging. The second gel body 1004b takes the form of a rod, a roll or layered roll, volute or spiral roll, or a tube, having two ends, with one end of the second gel body 1004b physically coupled to one end of the first gel body 1004a. FIG. 10 also shows an optional implementation of the composite marker 1000 optionally comprising an additional third gel body 1004c. The optional third gel body 1004c takes the form of a rod, a roll or layered roll, volute or spiral roll, or a tube, having two ends, with one end of the optional third gel body 1004c physically coupled to one end of the first gel body 1004a. The optional third gel body 1004c can optionally carry at least one contrast material 1003 in or on the third gel body 1004c detectable by a detection modality different than X-ray imaging and different from the second gel body 1004b.

FIGS. 11A and 11B show a portion of a composite marker 1100 according to at least one illustrated implementation. In particular, FIGS. 11A and 11B show a gel body 1104 with a first plurality of ultrasound reflective elements 1102a (only one called out) dispersed therein. The gel body 1104 and ultrasound reflective elements 1102a can be formed as part of manufacturing a composite marker 1100. Thus, FIGS. 11A and 11B illustrate an operation or act in manufacturing a composite marker 1100.

Figure 11C:
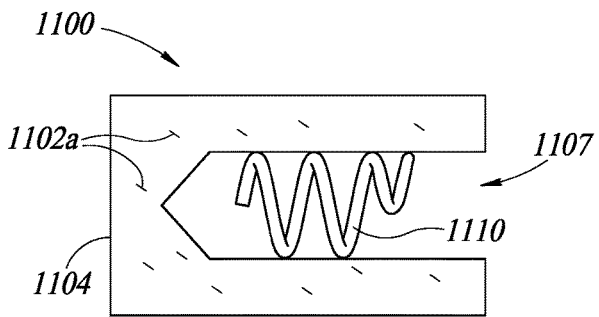
FIG. 11C is a side elevational view showing a portion of a composite marker according to at least one illustrated implementation, and in particular shows the gel body with the first plurality of ultrasound reflective elements of FIGS. 11A and 11B, with a cavity formed in the gel body and at least one radiopaque element, illustrated as a radiopaque wire or band, positioned in the cavity, the gel body, ultrasound reflective elements and the at least one radiopaque element which can be formed as part of manufacturing the composite marker.
Figure 11D:
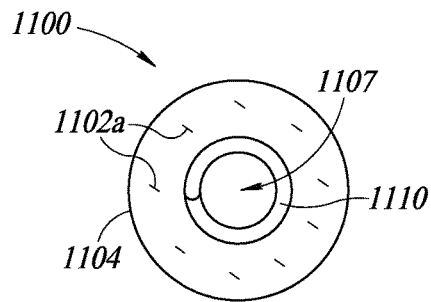
FIG. 11D is an end elevational view of the portion of the composite marker of FIG. 11C.

FIGS. 11C and 11D show a portion of a composite marker 1100 according to at least one illustrated implementation. In particular, FIGS. 11C and 11D show the gel body 1104 with the first plurality of ultrasound reflective elements 1102a of FIGS. 11A and 11B, with a cavity or passage 1107 formed in the gel body 1104 and at least one radiopaque element, illustrated as a radiopaque wire or band 1110, positioned in the cavity or passage 1107. The gel body 1104, ultrasound reflective elements 1102a and the at least one radiopaque element 1110 can be formed as part of manufacturing the composite marker 1100. Thus, FIGS. 11C and 11D illustrate an operation or act in manufacturing a composite marker 1100, for example an operation or act that occurs subsequent to the operation or act illustrated in FIGS. 11A and 11B.

Figure 11E:
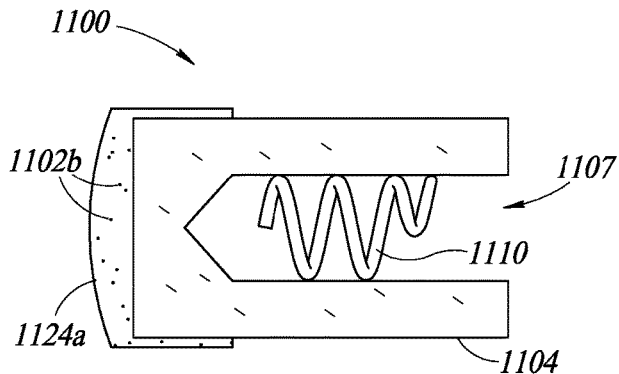
FIG. 11E is a side elevational view showing a portion of a composite marker according to at least one illustrated implementation, and in particular shows the gel body with the first plurality of ultrasound reflective elements and the at least one radiopaque element of FIGS. 11C and 11D, with a cap attached at an end of the gel body as an end cap, and with a second plurality of ultrasound reflective elements dispersed in the end cap, the gel body, ultrasound reflective elements, the at least one radiopaque element, and end cap which can be formed as part of manufacturing the composite marker.
Figure 11F:
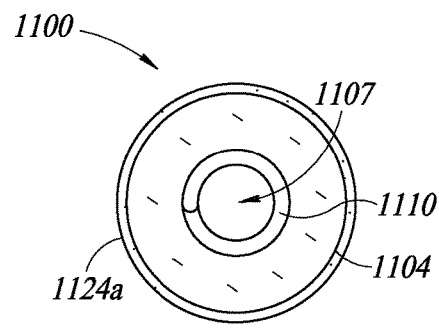
FIG. 11F is an end elevational view of the portion of the composite marker of FIG. 11E.

FIGS. 11E and 11F show a composite marker 1100 according to at least one illustrated implementation. In particular, FIGS. 11E and 11F show the gel body 1104 with the first plurality of ultrasound reflective elements 1102a and the at least one radiopaque element 1110 of FIGS. 11C and 11D, with a cap attached at an end 1104a of the gel body 1104 as an end cap 1124a. The end cap 1124a may include a second plurality of ultrasound reflective elements 1102b dispersed in the end cap 1124a. The gel body 1104, ultrasound reflective elements 1102a, 1102b, the at least one radiopaque element 1110, and end cap 1124a can be formed as part of manufacturing the composite marker 1100. Thus, FIGS. 11E and 11F illustrate an operation or act in manufacturing a composite marker 1100, for example an operation or act that occurs subsequent to the operation or act illustrated in FIGS. 11C and 11D.

While FIG. 11E shows the end cap 1124a positioned over an already closed end of the gel body 1104, in some implementations the end cap 1124a may be positioned over an open end of the gel body 1104. Also, while FIG. 11E shows the gel body as having one open end and one closed end, in some implementations the gel body may have two open ends which are closed by respective end caps 1124a, 1124b (see FIG. 11G), or two closed ends, one or both of which may include respective end caps 1124a, 1124b (see FIG. 11G).

Figure 11G:
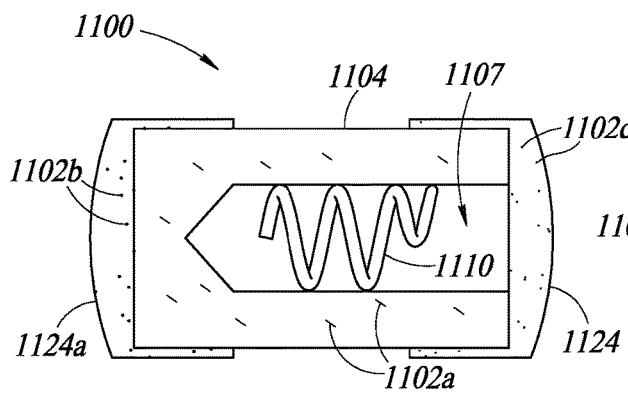
FIG. 11G is a side elevational view showing a composite marker according to at least one illustrated implementation, and in particular shows the gel body with the first plurality of ultrasound reflective elements, at least one radiopaque element, with a respective end cap attached at respective ends of the gel body with respective pluralities of ultrasound reflective elements dispersed in the end caps.

FIG. 11G show a composite marker 1100 according to at least one illustrated implementation. In particular, FIG. 11G shows a gel body 1104 with the first plurality of ultrasound reflective elements 1102a, the at least one radiopaque element 1110, and end cap 1124a of FIGS. 11E and 11F, and adds a second end cap 1124b with a third plurality of ultrasound reflective elements 1102c dispersed therein positioned at the other end 1104b of the gel body 1104. While illustrated as having the same overall shape and size as one another, one of the end caps 1124a may have a different size and shape than the other one of the end caps 1124b, which may facilitate detection of pose (e.g., position and orientation) of a composite marker 1100 within a portion of bodily tissue. The gel body 1104, ultrasound reflective elements 1102a, 1102b, 1102c, the at least one radiopaque element 1110, and end caps 1124a, 1124b can be formed as part of manufacturing the composite marker 1100. Thus, FIG. 11G illustrates an operation or act in manufacturing a composite marker 1100, for example an operation or act that occurs subsequent to the operation or act illustrated in FIGS. 11C and 11D.

With respect to the implementations of FIGS. 11E, 11F and 11G, the end cap(s) 1124a, 1124b may advantageously have different physical properties from the gel body 1104. For example, the end cap(s) 1124a, 1124b may be formed of a different material that the gel body 1104. For instance, the end caps 1124a, 1124b may be formed of a polyethylene glycol (PEG) while the gel body 1104 may be formed of a gelatin. Also for instance, the end caps 1124a, 1124b may have a different degree or extensiveness of cross-linking than that of the gel body 1104. Additionally or alternatively, the end caps 1124a, 1124b may have a different type and/or distribution of ultrasound reflective elements 1102b, 1102c than a type and/or distribution of ultrasound reflective elements 1102a in the gel body 1104. Additionally or alternatively, the end cap(s) 1124a, 1124b may advantageously have different physical properties from one another, for instance formed of different materials from one another, different levels or extensiveness of cross-linking from one another and/or different types and/or distributions of ultrasound reflective elements 1102b, 1102c from one another. Any one or more of the components of the composite maker 1100 may include none, one, or more types of contrast material to provide detectability via modalities in addition to ultrasound and X-ray.

Figure 11H:
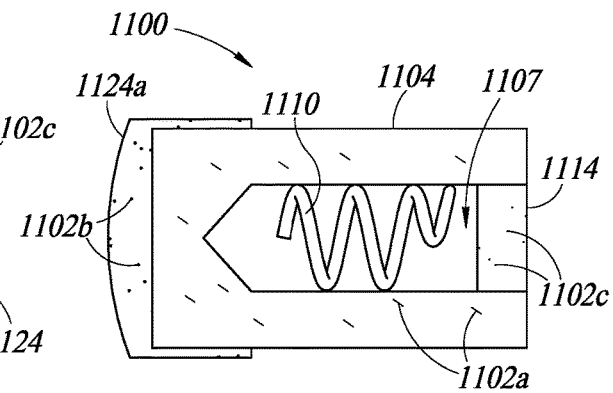
FIG. 11H is a side elevational view showing a composite marker according to at least one illustrated implementation, and in particular shows the gel body with the first plurality of ultrasound reflective elements, at least one radiopaque element, with an end cap attached at one end of the gel body and a gel plug attached at another end of the gel body, the end cap and gel plug with respective pluralities of ultrasound reflective elements dispersed therein.

FIG. 11H show a composite marker 1100 according to at least one illustrated implementation. In particular, FIG. 11H shows a gel body 1104 with the first plurality of ultrasound reflective elements 1102a, the at least one radiopaque element 1110, and end cap 1124a of FIGS. 11E and 11F, and adds a gel plug 1114 with a third plurality of ultrasound reflective elements 1102c dispersed therein positioned at the other end 1104b of the gel body 1104. The gel body 1104, ultrasound reflective elements 1102a, 1102b, 1102c, the at least one radiopaque element 1110, the end cap 1124a, and the gel plug 1114 can be formed as part of manufacturing the composite marker 1100. Thus, FIG. 11H illustrates an operation or act in manufacturing a composite marker 1100, for example an operation or act that occurs subsequent to the operation or act illustrated in FIGS. 11C and 11D.

With respect to the implementation of FIG. 11H, the end cap 1124a may advantageously have different physical properties from the gel body 1104 and/or the gel plug 1114. For example, the end cap 1124a may be formed of a different material that the gel body 1104 and/or gel plug 1114. For instance, the end cap 1124a may be formed of a polyethylene glycol (PEG) while the gel body 1104 and/or gel plug 1114 may be formed of a gelatin. Also for instance, the end cap 1124a may have a different degree or extensiveness of cross-linking than that of the gel body 1104 and/or gel plug 1114. Additionally or alternatively, the end cap 1124a may have a different type and/or distribution of ultrasound reflective elements 1102b than a type and/or distribution of ultrasound reflective elements 1102a in the gel body 1104 and/or the ultrasound reflective elements 1102c in the gel plug 1114. Additionally or alternatively, the gel body 1104 and the gel plug 1114 may advantageously have different physical properties from one another, for instance formed of different materials from one another, different levels or extensiveness of cross-linking from one another different rates of hydration and/or associated swelling, and/or different types and/or distributions of ultrasound reflective elements 1102a, 1102c from one another. Any one or more of the components of the composite maker 1100 may include none, one, or more types of contrast material to provide detectability via modalities in addition to ultrasound and X-ray.

The different physical properties of the portions of the composite maker 1100, whether due to one or more of different materials, different degrees or extensiveness of cross-linking, different type and/or distribution of ultrasound reflective elements, may provide distinct advantages over a homogenous composite marker. Such may, for example, provide for different responses to ultrasound energy be the different portions of the composite maker 1100. For instance, a particular material and/or more highly cross-linked portion producing a different return signal than different material and/or a relatively less highly cross-linked portion. For instance, one portion containing ultrasound reflective particles may comprise a first gel material or be cross-linked to provide a relative better response during Doppler mode ultrasound operation than another portion, while another portion containing ultrasound reflective particles may comprise a second gel material and/or be cross-linked to provide a better response during B-mode ultrasound operation than another portion. Such may additionally or alternatively, for example, provide for different rates of hydration and/or swelling of the different portions of the composite maker 1100, a PEG portion hydrating and swelling more quickly than a gelatin portion, allowing quick detection of a portion of the composite marker after initial insertion into the body while also providing for relatively long persistence allowing detection of another portion of the composite marker long (e.g., months) after initial insertion into the body. Such may additionally or alternatively, for example, provide for different durations of persistence of the different portions of the composite maker 1100, a synthetic material and/or more highly cross-linked portion persisting longer than a natural material and/or relatively less highly cross-linked portion.

Also for example, PEG may hydrate much more rapidly than, for instance gelatin or freeze-dried gelatin. Such may advantageously allow a PEG portion of the composite marker to be detectable via ultrasound very quickly after exposure to bodily fluids (e.g., on insertion or implantation during a biopsy), as compared to a gelatin portion of the composite marker. The gelatin portion of the composite marker may take a longer time to become hydrated and detectable, but may advantageously persist over an extended period of time, allowing the composite marker to be detectable via ultrasound during a surgical procedure even months after initial insertion (e.g., insertion during the biopsy). The use of ultrasound throughout the lifecycle of the composite marker may be particularly advantageous with respect to cost, time, personnel, and safety as compared to the use of ionizing radiation for imaging.

The composite marker 900, 1000, and/or 1100 also comprises at least one radiopaque element (e.g., radiopaque wire or band, radiopaque clip) 910, 1010, 1110 carried in or on the first gel body 904a, 1004a, 1104, which comprises a radiopaque material, detectable via X-ray imaging (e.g., computed tomography, fluoroscopy).

All above descriptions and implementations discussed or illustrated relating to the at least one radiopaque element (e.g., radiopaque wire or band 110, radiopaque clip), including suitable radiopaque materials for the at least one radiopaque element, and the form, shape, and size of the at least one radiopaque element, are all applicable to the embodiment(s) or implementation(s) relating to the at least one radiopaque element (e.g., radiopaque wire or band 910, 1010, 1110, or radiopaque clips (see FIGS. 4F-4I) in the composite marker 900, 1000, 1100.

The composite marker 900, 1000, 1100 also comprises a first gel body 904a, 1004a, 1104, and optionally a second gel body 904b, 1004b, and optionally additional gel bodies (such as 1004c, 1114), which may comprise a natural gelatinous material, a synthetic polymer, or a combination thereof.

All above descriptions and implementations discussed or illustrated relating to the gel body 104, including suitable materials for the gel body, crosslinking of the gel body, the form and size of the gel body, and the preparation of the gel body, are all applicable to the implementation(s) relating to the gel bodies (including the first gel body 904a, 1004a, 1104, a second gel body 904b or 1004b, or optionally additional gel bodies such as 1004c, 1114) in the respective composite marker 900, 1000, 1100.

The first gel body, for instance, the first gel body 904a, 1004a, 1104 in respective composite marker 900, 1000, 1100, may take a variety of forms, for example depending on the mold or mandrel used when molding or otherwise forming the gel body. In some embodiments, the first gel body 904a, 1004a, 1104 may take the form of a tube (as shown in FIG. 7B), a roll, r layered roll, volute or spiral roll (as shown in FIGS. 8A-8C), or a rod (as shown in FIG. 6A).

The second gel body 1004b and each of the optionally additional gel bodies (such as 1004c, 1114) in the composite marker 1000, 1100 may take a variety of forms, for example depending on the mold or mandrel used when molding or otherwise forming the gel body. In some implementations, the second gel body 1004b and each of the optionally additional gel bodies (such as 1004c, 1114) may take the form of a tube (as shown in FIG. 7B), a roll, layered roll, volute or spiral roll (as shown in FIGS. 8A-8C), or a rod (as shown in FIG. 6A).

In some implementations, the first gel body does not contain any contrast material. For instance, the first gel body 904a in the composite marker 900 does not contain any contrast material. For instance, the first gel body 1004a in the composite marker 1000 does not contain any contrast material.

The second gel body, for instance, the second gel body 904b, 1004b in respective composite marker 900, 1000, comprises at least one contrast materials 903 or 1003. Each of the optionally additional gel bodies (such as 1004c, 1114) may also comprise at least one contrast material 1003. The contrast material 903, 1003 may include two or more different contrast materials, each detectable by a respective detection modality that is different from one another and different than X-ray imaging.

In some implementations, the contrast material 903, 1003 comprises a plurality of ultrasound reflective elements 102 each respectively comprising a body having at least one cavity and at least one fluid in the at least one cavity to provide reflectivity of ultrasound imaging signals. In these implementations, all above descriptions and embodiments relating to the ultrasound reflective element 102, including the variety of forms that the ultrasound reflective element 102 takes, the shape and materials of the body of the ultrasound reflective element 102a, the techniques for form the ultrasound reflective element, the fluid 105 entrapped in the cavity of the ultrasound reflective element, the coating 106 on the ultrasound reflective element, the size of the ultrasound reflective element, and the exemplary embodiments shown in FIGS. 1B-1C and FIGS. 2A-2D, are all applicable to the implementation(s) relating to the contrast material 903 or 1003 in the respective composite marker 900, 1000, 1100.

In some implementations, the contrast material 903 or 1003 comprises visually detectable materials such as a dye or a pigment. Suitable visually detectable materials have been discussed above relating to the contrast material 103.

In some implementations, the contrast material 903 or 1003 comprises a material detectable via magnetic resonance imaging (MRI). Suitable MRI-detectable materials have been discussed above relating to the contrast material 103.

In some implementations, the contrast material 903 or 1003 comprises a radioactive material, detectable via nuclear-based imaging (e.g., scintigraphy, positron emission tomography, or single-photon emission computed tomography). Suitable radioactive materials have been discussed above relating to the contrast material 103.

In some implementations, when one or more contrast material 903 or 1003 is present in or on a gel body (e.g., the second gel body 904b or 1004b or the optionally additional gel bodies, such as 1004c, 1114), the contrast material 903 or 1003 is carried in or on in a dispersion therein, optionally in a colloidal dispersion (see the exemplary embodiments illustrated in FIG. 1A and FIG. 5A).

When the contrast material 903 or 1003 is dispersed in the gel body (e.g., gel body 104, 1104, the second gel body 904b or 1004b or the optionally additional gel bodies, such as 1004c, 1114), the contrast material may also further comprise a coating or encapsulation of a shell, to prevent the contrast material from effusing out of the gel body. The coating or encapsulation of a shell can be formed from a variety of inorganic materials. Suitable inorganic materials have been discussed above relating to the contrast material 103 and the optional coating or encapsulation of a shell 107.

In some implementations, when two or more contrast materials are present in or on a gel body (e.g., gel body 104, 1104, the second gel body 904b or 1004b or the optionally additional gel bodies, such as 1004c), one contrast material may be carried on or embedded in another contrast material. For instance, the two or more contrast materials present in or on a gel body may comprise a fluorescent dye 503, and the fluorescent dye may be carried on or embedded in another contrast material 502 (see the exemplary embodiment illustrated in FIG. 5B).

In at least one implementation, the two or more contrast materials present in or on a gel body comprise a fluorescent dye 503 and a plurality of ultrasound reflective elements 502 (or 102), each respectively comprising a body having at least one cavity containing entrapped fluid (gas or liquid) 105 to provide reflectivity of ultrasound imaging signals, and the fluorescent dye 503 may be carried on or embedded in the contrast material 502 (or 102) (see the exemplary embodiments illustrated in FIG. 5B and FIGS. 2A-2D).

In the implementations relating to composite markers 100, 500a, 500b, 900, 1000, 1100, each gel body of the composite marker 100, 500, 900, 1000, 1100 may be expandable, for example when implanted into bodily tissue. The gel body of the composite marker may be able to hydrate rapidly, achieving full hydration when disposed within an aqueous environment within 24 hours in some cases.

In some implementations, each gel body of the composite marker 100, 500a, 500b, 900, 1000, 1100 may, in an unexpanded state, have a length of about 2 mm to about 40 mm and a transverse dimension of about 0.5 mm to about 2 mm. The gel body of the composite marker 100, 500a, 500b, 900, 1000, 1100 may have a ratio of size expansion from a dried unexpanded state to a water saturated expanded state of about 1:1.5 to about 1:10. The gel body of the composite marker 100, 500a, 500b, 900, 1000, 1100 may have a ratio of size expansion from a dried unexpanded state to a water saturated expanded state of about 1:2 to about 1:3.

In some implementations, each gel body of the composite marker 100, 500a, 500b, 900, 1000, 1100 may have an axial length of about 1 cm to about 10 cm, for instance, from about 2 cm to about 8 cm. In an exemplary implementation, an outer transverse dimension of the gel body molded in a 2 mm silicone tube may be about 0.025 to about 0.031 inches, about 0.026 to about 0.030 inches, or about 0.027 to about 0.028 inches. The gel body may have a dry weight of about 7 to about 7.8 mg and in some cases, an axial length of about 22 mm to about 24 mm. Upon soaking the composite marker in water, the gel body may expand to an outer transverse dimension of about 1.5 mm with an axial length of about 23 mm to about 25 mm in some cases. In an exemplary implementation, an outer transverse dimension of the gel body molded in 2.4 mm silicone tubes may be about 0.026 to about 0.034 inches, about 0.029 to about 0.033 inches, or about 0.031 to about 0.032 inches after being freeze dried and subsequently compressed. The gel body may have a dry weight of about 6.2 mg to about 8 mg.

In some implementations, the composite marker 100, 500a, 500b, 900, 1000, 1100 may have a pellet shape, i.e., having a relatively shorter axial length. For instance, the gel body may have a transverse dimension of about 1 mm to about 3 mm and an axial length of about 2 mm to about 10 mm.

A method for forming a composite marker may comprise: incorporating at least one radiopaque element (e.g., radiopaque wire or band, radiopaque clip) to a gel body, and casting the gel body incorporating the at least one radiopaque wire or band to form the composite marker. A method for forming a composite marker may comprise: casting a gel body, and incorporating at least one radiopaque element to the gel body to form the composite marker. The method may further comprise, prior to incorporating and/or casting, mixing a gel or gel forming material with at least one contrast material detectable via a detection modality different than X-ray imaging, to result in a gel body carrying the at least one contrast material in or on the gel body.

All above descriptions and implementations discussed or illustrated in the above aspect relating to the composite marker (100, 500a, 500b, 900, 1000, 1100), including descriptions and implementations relating to the gel or gel forming material in relation to the gel body (104, 504, 1104, first gel body, second gel body, and additional gel bodies), the at least one radiopaque element (110, 510, 910, 1010, 1110), and the at least one contrast material (ultrasound reflective element 102, fluorescent dye 503, and other contrast materials 103), are all applicable to a method for forming a composite marker.

The at least one radiopaque element (e.g., radiopaque wire or band, radiopaque clip) may be commercially available and may need minimum treatment before incorporating to the gel body to form the composite marker.

Alternatively, the method may further comprise forming the at least one radiopaque element (e.g., radiopaque wire or band, radiopaque clip) from a liquid or colloidal suspension containing a radiopaque material. Suitable radiopaque materials have been discussed above relating to the at least one radiopaque wire or band 110. This may be used when the radiopaque material is not in a wire or band form, e.g., many oxide or salt forms of the radiopaque metal exist in powder or particulate form.

In some implementations, the forming the at least one radiopaque element (e.g., radiopaque wire or band, radiopaque clip) comprises dissolving or suspending the radiopaque material in a gel or gel forming material comprising a natural gelatinous material, a synthetic polymer, or a combination thereof, same or different than the gel or gel forming material that results in the gel body of the composite marker, thereby forming a liquid or colloidal suspension containing the radiopaque material. Suitable gel or gel forming materials have been discussed above relating to the gel body 104. The forming the at least one radiopaque wire or band further comprises spinning or drawing a fiber or band from the liquid or colloidal suspension containing the radiopaque material.

The gel or gel forming material may be prepared from mixing a dry gel or gel forming material with distilled water in a variety of concentrations, for example, in a concentration of about 1 wt % (i.e., 1 g gel or gel forming material per 100 ml distilled water) to about 50 wt %, such as about 1 wt % to about 10 wt %, about 4 wt % to about 10 wt %, or about 4 wt % to about 6 wt %. The radiopaque material may be added in a concentration of about 1 wt % (i.e., 1 g radiopaque material per 100 ml distilled water) to about 50 wt %.

In some implementations, the forming the at least one radiopaque element (e.g., radiopaque wire or band, radiopaque clip) comprises spinning or drawing a fiber or band from a liquid or colloidal suspension that is aqueous, containing about 1-50 wt % gel or gel forming material and about 1-50 wt % radiopaque material.

In at least one implementation, the radiopaque material is barium sulfate. In at least one embodiment, the gel or gel forming material is PVA or PEG.

In at least one implementation, the forming the at least one radiopaque element (e.g., radiopaque wire or band, radiopaque clip) comprises spinning or drawing a fiber or band from a liquid or colloidal suspension that is aqueous, containing about 1-5% hydrolyzed PVA and about 1-5% barium sulfate.

In at least one implementation, the forming the at least one radiopaque element (e.g., radiopaque wire or band, radiopaque clip) comprises spinning or drawing a fiber or band from a liquid or colloidal suspension that is aqueous, containing about 40-50% hydrolyzed PVA and about 40-50% barium sulfate.

In an exemplary implementation for forming a radiopaque element (e.g., radiopaque wire or band, radiopaque clip), 5 wt % PVA aqueous solution (99% hydrolyzed; MW 78,000) is prepared by dissolving PVA in distilled water. 5 wt % barium sulfate powder is added to this PVA solution and is stirred to a complete mixing. A fiber is spun or drawn by slowly dispensing this solution/colloidal suspension through a spinneret nozzle. The resulting fiber or band or clip is dried by either natural evaporation or by forced air to accelerate drying.

Optionally, at least one other contrast material may be added to the liquid or colloidal suspension when forming the at least one radiopaque wire or band or radiopaque clip. In this case, the formed radiopaque wire or band will itself contain at least one other contrast material.

The resulting fiber or band or clip may be at least partially cross-linked by a physical process or a chemical modification (with or without using a crosslinking agent). Suitable crosslinking processes and crosslinking agents have been discussed above relating to the gel body 104. In at least one implementation, the resulting fiber or band or clip may be at least partially cross-linked by freezing and/or thawing. In at least one implementation, the resulting fiber or band or clip is rendered at least partially cross-linked by using a crosslinking agent.

The resulting fiber or band or clip may be shaped to any desired shape, for example, a straight line, helix, open coil, closed coil, serpentine loop, lemniscate, circle, wavy circle, T-shaped, U-shaped, V-shaped, W-shaped, etc. The shaping may occur before or after the crosslinking.

In some implementations, the method may further comprise, prior to incorporating and/or casting or wrapping, mixing a gel or gel forming material with at least one contrast material detectable via a detection modality different than X-ray imaging, to result in a gel body carrying the at least one contrast material in or on the gel body.

In some implementations, the at least one contrast material comprises two or more different contrast materials. In at least one implementation, the two or more different contrast materials comprise a plurality of ultrasound reflective elements. The plurality of ultrasound reflective elements may be mixed with at least one other contrast material first, so that at least one other contrast material may be carried by the ultrasound reflective elements. The plurality of ultrasound reflective elements may also be mixed with at least one other contrast material during the process of preparing the ultrasound reflective elements, so that the at least one other contrast material may be carried by the ultrasound reflective elements. Mixing may infuse the at least one other contrast material into the cavity of the ultrasound reflective element. Mixing may infuse the at least one other contrast material in the body of the ultrasound reflective element. The plurality of ultrasound reflective elements carrying at least one other contrast material are then mixed with the gel or gel forming material to result in a gel body carrying the plurality of ultrasound reflective elements and at least one other contrast material in or on the gel body.

In some implementations, at least one contrast material and the gel or gel forming material are mixed together in one operation or act, so that the contrast material may be carried in or on the gel body in a dispersion therein, optionally in a colloidal dispersion.

In some implementations, all the contrast materials and the gel or gel forming material are all mixed together in one operation or act, so that all the contrast material may be carried in or on the gel body in a dispersion therein, optionally in a colloidal dispersion.

In some implementations, the at least one contrast material comprises a fluorescent dye materials. The mixing may further comprise exposing the fluorescent dye to the gel or gel forming material to form an activated and/or hydrolyzed fluorescent dye, carried in or on the gel body.

In some implementations, mixing a gel or gel forming material with at least one contrast material includes mixing a liquid or colloidal suspension containing about 1-20% gel or gel forming material and at least one contrast material at about 1-5 mg/ml.

In at least one implementations, the gel or gel forming material is PVA or PEG. In at least one implementation, the at least one contrast material comprises a plurality of hollow silica shells.

In at least one implementation, mixing a gel or gel forming material with at least one contrast material includes mixing an aqueous solution or aqueous colloidal suspension containing about 5-10% hydrolyzed PVA with the at least one contrast material comprising a plurality of hollow silica shells at about 1-3 mg/ml.

The method may further comprise carrying out a physical process or a chemical modification to the gel body to at least partially crosslink the gel body.

In some implementations, the method further comprises drying (e.g., freeze-drying, critical point drying, or air drying), thermo-dehydrating, or radiating (e.g., UV radiating or γ-ray radiating) to at least partially crosslink the gel body. In at least one implementation, the method further comprises freezing and/or thawing to at least partially crosslink the gel body.

In some implementations, the method further comprises adding a crosslinking agent to the gel or gel forming material to at least partially crosslink the gel body. Suitable crosslinking agents have been discussed above.

In some implementations, two or more same or different crosslinking processes may be carried out at various stages of the method. For instance, one crosslinking process may be carried out to the gel body prior to incorporating and/or casting or wrapping, to at least partially crosslink the gel body, and more crosslinking process(es) (which may be the same or different than the previous crosslinking process) may be carried out to the gel body after incorporating and/or casting or wrapping, to at least partially crosslink the gel body.

In some implementations, the method may further comprise molding/casting the gel body by a mold or mandrel based on the shape desired (e.g., a tubular mold, or a mandrel). For instance, the gel body may be molded into an inner cylindrical cavity of a silicone tube; the gel body may be frozen and/or freeze dried; the gel body may be pushed out of the inner cylindrical cavity; and the gel body may be pressed (or compressed) to remove air and reduce the volume and outer profile such that the composite marker will fit in an inner lumen of a cannula of a syringe applicator. The gel body may also be compressed and de-aired after being freeze-dried while still disposed within an inner lumen of a silicone tube. In some implementations, the freeze-dried gel bodies may be compressed by rolling the freeze-dried gel bodies between two silicone sheet surfaces to remove air pockets and reduce profile.

The freeze dried gel body may then be removed from the mold (e.g., silicone tube), and may be sized and configured to fit into a various size syringe applicator device (e.g., standard 14-guage, or 19- or 20-gauge) with sufficient interference for an accurate and timely deployment.

As another example, the gel body may be molded or cast over a mandrel or rolled about an outer perimeter (e.g., outer diameter) of a mandrel. The mandrel may take any desired shape or form. For instance, a pre-shaped and/or pre-cut gel body may be positioned over or wrapped around or partially around a mandrel; the gel body and the mandrel may be pressed against each other so that the mandrel extends entirely through the longitudinal axis of the gel body to form a hollow tube within the gel body with both ends open, or the mandrel extends partially through the longitudinal axis of the gel body to form a hollow interior within the gel body with one end open and one end closed; the gel body may be frozen and/or freeze dried, for example prior to or after being wrapped about the mandrel.

The total amounts of all types of contrast materials (including ultrasound reflective elements, fluorescent dye, and other contrast materials) and gel or gel forming material for forming gel body may be used in a ratio ranging from about 0.1 mg/ml (i.e., 0.1 mg contrast material per 1 ml gel or gel forming material) to about 10 mg/ml, for instance, from about 0.1 mg/ml to about 8 mg/ml, or from about 2 mg/ml to about 5 mg/ml.

The at least one radiopaque element (e.g., radiopaque wire or band, radiopaque clip) may be incorporated to the gel body by a wide variety of manners depending on the position the radiopaque element takes relative to the gel body. For instance, the at least one radiopaque wire or band may be wrapped around the outer surface of the gel body, or the radiopaque wire band or clip embedded in the gel body, dropped to the interior cavity of the gel body, etc.

The at least one radiopaque element may be incorporated to the gel body before or after the gel body is cast/molded, before or after the gel body is cross-linked (e.g., by freezing and/or freeze-drying), before or after the gel body is pressed (or compressed), and before or after the gel body is rolled.

In an exemplary implementation, the composite marker illustrated in FIGS. 7A and 7B can be prepared by casting a gel body (e.g., gelatin) containing a plurality of hollow silica shells to a fillable tube. The tube is then freeze-dried. A radiopaque element (e.g., radiopaque wire or band) is positioned in the hollow interior of the freeze-dried tube. The tube is then optionally sealed at one end or both ends with a gel or gel forming material. The freeze-drying may also be carried out after the tube is sealed. Optionally, one or more end caps 1124a, 1124b may be applied.

In an exemplary implementation, a composite marker can be prepared by casting a gel body (e.g., gelatin) containing a plurality of hollow silica shells as a sheet. The sheet is then molded or cast into a desired shape. The sheet may be wrapped about an outer perimeter of a mandrel. The sheet and the mandrel may be pressed against each other to form the gel sheet as a hollow tube. The mandrel may extend entirely along a longitudinal axis of the gel sheet, extending past either edge thereof such that the hollow tube is formed with both opposing ends open. Alternatively, the mandrel extends partially along the longitudinal axis of the gel sheet, extending past only one edge thereof such that the hollow tube is formed with one end open and the opposing end closed. The gel sheet may then be frozen and/or freeze dried. Alternatively, the gel sheet may be frozen and/or freeze dried prior to being wrapped about the mandrel. A radiopaque element (e.g., radiopaque wire or band, radiopaque clip) is positioned in the hollow interior of the freeze-dried gel body. The open end(s) of the gel body may be optionally sealed with a gel or gel forming material. The freeze-drying may also be carried out after the end(s) of the gel body is sealed.

In an exemplary implementation, the composite marker illustrated in FIGS. 8A-8C can be prepared by casting a gel body (e.g., gelatin) containing a plurality of hollow silica shells to a U-shape (FIG. 8A) open roll. The tube is then freeze-dried. A radiopaque element (e.g., radiopaque wire or band, radiopaque clip) is dropped to the interior cavity of the freeze-dried roll. The roll is then optionally pressed and/or rolled to close or partially close the opening of the roll, forming either the shape in FIG. 8B or in FIG. 8C. The radiopaque element may only occupy a portion of the roll (axially), and the ends of the roll without being occupied by the radiopaque element may be crushed or crimped. The freeze-drying may also be carried out after the radiopaque element is dropped in the roll.

In an exemplary implementation, the composite marker illustrated in FIGS. 9A-9B can be prepared by casting a first gel body (e.g., gelatin) to a rod, which is then freeze-dried. A radiopaque element (e.g., radiopaque wire or band, radiopaque clip) is wrapped around the outer surface of the first gel body. The first gel body is then mixed with a gel or gel forming material containing a plurality of hollow silica shells and cast to a rod, forming a second gel body with the first gel body and the radiopaque wire or band inside the second gel body. The second gel body is then freeze-dried.

A method of marking a target site in a mammalian subject may comprise: administering parenterally to the target site in the mammalian subject a composite marker comprising: a gel body having an outer surface; a plurality of ultrasound reflective elements carried in or on the gel body, each ultrasound reflective element respectively comprising a body having at least one cavity and at least one fluid in the at least one cavity to provide reflectivity of ultrasound imaging signals; and at least one radiopaque element (e.g., radiopaque wire or band, radiopaque clip) carried in or on the gel body, wherein the at least one radiopaque element not disposed around the outer surface of the gel body. The method also comprises detecting the target site and the composite gel marker with ultrasound imaging or X-ray imaging.

All above descriptions and implementations discussed or illustrated in the above aspect relating to the composite marker 100, including descriptions and embodiments relating to the ultrasound reflective element 102, the at least one radiopaque element (e.g., radiopaque wire or band 110, radiopaque clip), and the gel body 104, are all applicable to a method marking a target site in a mammalian subject.

In some implementations, the target site comprises a tumor. The method further comprises surgically excising the tumor using ultrasound imaging or X-ray imaging as a detecting guidance, wherein the detecting guidance is different than the detection modality used in the detecting the target site and the composite gel marker.

A method of marking a target site in a mammalian subject may comprise: administering parenterally to the mammalian subject a composite marker, comprising: a gel body having an outer surface; an activated and/or hydrolyzed fluorescent dye carried in or on the gel body; and at least one radiopaque element (e.g., radiopaque wire or band, radiopaque clip) carried in or on the gel body, wherein the at least one radiopaque element not disposed around the outer surface of the gel body. The method also comprises detecting the target site and the composite gel marker with X-ray imaging or a detection modality that detects fluorescence.

All above descriptions and implementations discussed or illustrated in the above aspect relating to the composite marker 500a, 500b, including descriptions and implementations relating to the fluorescent dye 503, the at least one radiopaque element (e.g., radiopaque wire or band 510, radiopaque clip), and the gel body 504, are all applicable to a method marking a target site in a mammalian subject.

In some implementations, the target site comprises a tumor. The method further comprises surgically excising the tumor using X-ray imaging or a detection modality that detects fluorescence as a detection guidance, wherein the detection guidance is different than the detection modality used in the detecting the target site and the composite gel marker.

A method of marking a target site in a mammalian subject may comprise: administering parenterally to the mammalian subject a composite marker, comprising: a first gel body having an outer surface; at least one radiopaque element (e.g., radiopaque wire or band, radiopaque clip) disposed around and contacting at least a portion of the outer surface of the first gel body, and a second gel body carrying at least one contrast material in or on the second gel body detectable by a detection modality different than X-ray imaging, the second gel body physically coupled to the first gel body. The method also comprises detecting the target site and the composite gel marker with X-ray imaging or a detection modality capable of detecting the at least one contrast material.

All above descriptions and implementations discussed or illustrated in the above aspect relating to the composite marker 900, 1000, 1100, including descriptions and embodiments relating to the gel body 1104, the first gel body 904a or 1004a, the second gel body 904b or 1004b, the at least one radiopaque element (e.g., radiopaque wire or band 910 or 1010, radiopaque clip), and the at least one contrast material 903 or 1003, are all applicable to a method marking a target site in a mammalian subject.

In some implementations, the target site comprises a tumor. The method further comprises surgically excising the tumor using X-ray imaging or a detection modality capable of detecting the at least one contrast material as a detection guidance, wherein the detection guidance is different than the detection modality used in the detecting the target site and the composite gel marker.

In all these implementations relating to a method of marking a target site in a mammalian subject, the composite marker may be administered to the target site in a mammalian subject parenterally via any administration route known to one skilled in the art. For instance, parenteral administration of the composite marker can be performed by injection, for example, by using a needle and a syringe, or by the insertion of an indwelling catheter. In this case, the size and shape of the composite marker can be adjusted to fit in the internal size and shape of the needle, syringe, or catheter. More detailed descriptions about specific techniques that may be used for administering and delivering a gelatin marker to a tissue and suitable applicators may be found, for example in U.S. patent application Ser. No. 15/946,479, which is incorporated herein by reference in its entirety.

Unless otherwise indicated, use of the term "detecting" or "detection of" a composite marker herein refers to recognition of a return signal from a composite marker that is distinct from a return signal of tissue (or other material) at the target site surrounding or adjacent to the composite marker. For example, direct visual detection of a composite marker may include the ability of an observer to see the composite marker relative to the surrounding tissue due to a difference in color or fluorescence contrast, for example, between the marker and the surrounding tissue. A composite marker detected by ultrasound may reflect an ultrasound signal that is distinct in intensity, wavelength, phase, etc., relative to an ultrasound signal reflected by tissue surrounding or adjacent such a composite marker. In addition, effective detection in many cases does not need to include image projection onto a display screen for viewing by an operator such as is typically the case with fluoroscopic, ultrasonic, and magnetic resonance imaging (MRI). Detection of a composite marker may include reflection or return of some type of an energetic signal by the composite marker that may be projected from multiple points of origin to specify the location of a composite marker in three-dimensional space by methods such as triangulation. Such a technique may provide location information of the composite marker relative to the position of the multiple points of origin of the energetic signal. With regard to audio detection, an audible sound may be configured to increase in pitch, intensity, frequency or the like as a function of a probe's proximity to a composite marker and/or such a probe's appropriate directionality with respect to a composite marker.

In some instance, the composite marker are detected by two or more different detection modalities, either sequentially at different times or currently at the same time. Certain detection modalities, such as fluoroscopy, computed tomography (CT) imaging, and/or MRI, are used by a specialist such as a radiologist to identify the location of the tissue lesion. Certain different detection modalities, such as visual imaging (direct viewing of the markers by color or fluorescence) and/or ultrasound imaging (e.g., color flow Doppler ultrasound imaging) may be used by a specialist such as a surgeon to facilitate the subsequent therapeutic procedure, possibly during surgical removal or other type of treatment of the tissue lesion. Certain different detection modalities may be used to evaluate excised tissue after surgical removal from the patient or for any other suitable indication.

Implementations illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof, and various modifications are possible. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this disclosure.

The teachings of U.S. patent application Ser. No. 62/941,336, filed Nov. 27, 2019 and entitled "COMPOSITE TISSUE MARKERS DETECTABLE VIA MULTIPLE DETECTION MODALITIES"; Ser. No. 62/941,337, filed Nov. 27, 2019 and entitled "COMPOSITE TISSUE MARKERS DETECTABLE VIA MULTIPLE DETECTION MODALITIES INCLUDING RADIOPAQUE WIRE"; U.S. patent application Ser. No. 63/073,285, filed Sep. 1, 2020 and entitled "COMPOSITE TISSUE MARKERS DETECTABLE VIA MULTIPLE DETECTION MODALITIES INCLUDING RADIOPAQUE ELEMENT"; and U.S. patent application Ser. No. 15/946,479, are incorporated herein by reference in their entirety.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

We claim:
1. A composite marker, comprising:
a gel body having an outer surface, wherein the gel body is at least partially cross-linked to persist in a human body for at least 3 weeks;
a first plurality of sealed ultrasound reflective elements, each sealed ultrasound reflective element respectively comprising a porous particle having a respective outer surface, a respective plurality of cavities and a gas in the plurality of cavities to provide reflectivity of ultrasound imaging signals, wherein each ultrasound reflective element comprises a hydrophobic coating on the respective outer surface thereof that at least temporarily seals respective pores thereof with the gas entrapped therein, the hydrophobic coating comprises a mono-, di-, tri-, or tetra-alkoxysilane; and
at least one radiopaque element carried in or on the gel body, wherein the at least one radiopaque element is not disposed around the outer surface of the gel body,
wherein the first plurality of sealed ultrasound reflective elements with the hydrophobic coating at least on the respective outer surface thereof are carried in a colloidal dispersion in the at least partially cross-linked gel body.

2. The composite marker of claim 1, wherein each porous particle comprises silica or titanium dioxide.

3. The composite marker of claim 1, wherein the gel body further comprises at least one or more contrast materials, each of the one or more contrast materials detectable via a respective detection modality that is different from one another and different than ultrasound imaging and X-ray imaging.

4. The composite marker of claim 3, wherein each of the one or more contrast materials includes at least one of: a dye or a pigment, visually detectable; a paramagnetic, superparamagnetic, ferrimagnetic or ferromagnetic compound, or a compound containing other non-zero spin nuclei than hydrogen, detectable via magnetic resonance imaging (MRI), or a radioactive material, detectable via nuclear-based imaging.

5. The composite marker of claim 1, wherein the at least one radiopaque element comprises at least one radiopaque wire or band takes the form of an open coil, closed coil, serpentine loop, lemniscate, or wavy circle.

6. The composite marker of claim 1, wherein the at least one radiopaque element comprises at least one radiopaque clip.

7. The composite marker of claim 6, wherein the at least one radiopaque clip has a bow-tie shape, a U-shape, or a dumbbell shape.

8. The composite marker of claim 1, wherein the gel body takes the form of a tube, a roll or layered or spiral roll, or a rod.

9. The composite marker of claim 1, wherein at least a portion of the at least one radiopaque element is embedded in the gel body.

10. The composite marker of claim 1, wherein the gel body takes the form of a hollow tube, and wherein the at least one radiopaque element is in a hollow interior of the hollow tube, with a pair of ends of the hollow tube sealed.

11. The composite marker of claim 1, further comprising:
   a gel end cap physically coupled at least proximate at least one end of the gel body.

12. The composite marker of claim 11, further comprising:
   a second plurality of ultrasound reflective elements carried in or on the gel end cap.

13. The composite marker of claim 11, wherein the gel end cap at least partially surrounds the outer surface of the gel body, and extends radially outwardly therefrom.

14. The composite marker of claim 13, wherein the gel end cap also extends longitudinally outwardly of an end of the gel body.

15. The composite marker of claim 11, wherein the gel body is comprised of a first material and the gel end cap is comprised of a second material, the second material different from the first material.

16. The composite marker of claim 15, wherein the gel body is comprised of a gelatin and the gel end cap is comprised of a polyethylene glycol.

17. The composite marker of claim 1, wherein the gel body forms a cavity in which the at least one radiopaque element is located, and a pair of opposed ends of the gel body are crimped to seal the cavity thereof.

18. The composite marker of claim 1, wherein the gel body forms a cavity in which the at least one radiopaque element is located, and the gel body is sized to close a respective opening at each of a pair of opposed ends of the gel body in response to the gel body hydrating when exposed to bodily fluids.

19. The composite marker of claim 1, wherein the gel body forms a cavity in which the at least one radiopaque element is located, and the gel body having an opening positioned at a first end thereof.

20. The composite marker of claim 19, further comprising:
   a gel plug positioned to close the opening at the first end of the gel body.

21. The composite marker of claim 20, further comprising:
   a gel end cap physically coupled at least proximate a second end of the gel body.

22. The composite marker of claim 1, wherein the radiopaque element comprises a radiopaque metal selected from the group consisting of stainless steel, platinum, gold, iridium, titanium, tantalum, tungsten, silver, rhodium, nickel, bismuth, and barium; an alloy of the radiopaque metals; an oxide of the radiopaque metals; a sulfate of the radiopaque metals; a carbonate of the radiopaque metals; or a combination thereof.

23. The composite marker of claim 1, wherein the radiopaque element comprises a radiopaque ceramic.

24. The composite marker of claim 1, wherein the gel body comprises a natural gelatinous material, a synthetic polymer, or a combination thereof.

25. The composite marker of claim 24, wherein the gel body comprises:
   i) a protein selected from the group consisting of collagen, gelatin, fibrin, fibronectin, and albumin;
   ii) a polysaccharide selected from the group consisting of cellulose or methyl cellulose, hyaluronic acid, chitin, chitosan, and calcium alginate;
   iii) a synthetic polymer selected from the group consisting of polyvinyl alcohol (PVA), polyglycolic acid (PGA), polylactic acid (PLA), poly(glycolic-co-lactic acid) (PLGA), polycaprolactone (PCL), polymethacrylate (PMA), polymethylmethacrylate (PMMA), polyethylene oxide (PEO), polyamine, polyoxaamide, polyoxaester, polyethylene glycol (PEG), polypropylene (PP), polytetrafluoroethylene (PTFE), polyester, polyetheretherketone (PEEK), and a copolymer thereof; or
   a mixture of any two or more members from i), ii), or iii).

26. The composite marker of claim 24, wherein the gel body is at least partially cross-linked via a physical process, a chemical modification, and/or using a crosslinking agent.

27. The composite marker of claim 26, wherein the gel body is rendered at least partially cross-linked by using a crosslinking agent selected from the group consisting of an aldehyde, glutaraldehyde, glyceraldehyde, dialdehyde, starch, epoxide, dimethyl adipimidate, glucosepane, carbodiimide, pentosidine, isocyanate or polyisocyanate, metallic cross-linker, ionic cross-linker, acrylic compound, alginate, sulfhydryl, genipin, and a combination thereof.

28. The composite marker of claim 26, wherein the gel body is rendered at least partially cross-linked by dry-freezing and thawing.

29. The composite marker of claim 26, wherein a degree of crosslinking of the gel body is pre-determined by a rate of degradation of the composite marker in a bodily tissue of the human body.

30. The composite marker of claim 29, wherein the rate of degradation of the composite marker in the tissues of the host mammalian subject is such that the composite marker persists in the tissues of the host mammalian subject for a period of about 9 months or longer.

31. The composite marker of claim 1, wherein the mono-, di-, tri-, or tetra-alkoxysilane of the hydrophobic coating is selected from: the group consisting of: propyltrimethoxysilane, hexyltrimethoxysilane, heptyltrimethoxysilane, octyltrimethoxysilane, nonyltrimethoxysilane, decyltrimethoxysilane, dodecyltrimethoxysilane, tridecyltrimethoxysilane, tetradecyltrimethoxysilane, pentadecyltrimethoxysilane, hexadecyltrimethoxysilane, heptadecyltrimethoxysilane, octadecyltrimethoxysilane, phenyltrimethoxysilane, propyltriethoxysilane, hexyltriethoxysilane, heptyltriethoxysilane, octyltriethoxysilane, nonyltriethoxysilane, decyltriethoxysilane, dodecyltriethoxysilane, tridecyltriethoxysilane, tetradecyltriethoxysilane, pentadecyltriethoxysilane, hexadecyltriethoxysilane, heptadecyltriethoxysilane, octadecyltriethoxysilane, phenyltriethoxysilane, methoxy (triethyleneoxy) propyltrimethoxysilane, 3-(methacryloyloxy) propyltrimethoxysilane, m, p-ethylphenethyltrimethoxysilane, 2-[methoxy (polyethyleneoxy) propyl]- trimethoxysilane, 3-aminopropyltrimethoxysilane, 3-mercaptopropyltrimethoxysilane, 3-isocyanatopropyltriethoxysilane, 3-isocyanatopropyltrimethoxysilane, and glycidoxypropyltrimethoxysilane.

32. The composite marker of claim 3, wherein each of the one or more contrast materials includes an activated and/or fluorescent dye or a pigment that is visually detectable and that is carried in or on the gel body.

* * * * *